(12) United States Patent
Scheller

(10) Patent No.: US 10,420,460 B2
(45) Date of Patent: Sep. 24, 2019

(54) ILLUMINATION PROBE

(71) Applicant: Katalyst Surgical, LLC, Chesterfield, MO (US)

(72) Inventor: Gregg D Scheller, Wildwood, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 186 days.

(21) Appl. No.: 15/671,219

(22) Filed: Aug. 8, 2017

(65) Prior Publication Data
US 2018/0070809 A1 Mar. 15, 2018

Related U.S. Application Data

(60) Provisional application No. 62/285,753, filed on Sep. 9, 2016.

(51) Int. Cl.
*A61B 3/00* (2006.01)
*A61B 3/12* (2006.01)
(Continued)

(52) U.S. Cl.
CPC .......... *A61B 3/0008* (2013.01); *A61B 3/1208* (2013.01); *A61B 3/135* (2013.01);
(Continued)

(58) Field of Classification Search
CPC ..... A61B 3/0008; A61B 3/1208; A61B 3/135; A61B 5/006; A61B 2090/3614; A61F 9/0007
See application file for complete search history.

(56) References Cited

U.S. PATENT DOCUMENTS 3,174,851 A 3/1965 Buehler et al.
4,122,853 A 10/1978 Smith
(Continued)

FOREIGN PATENT DOCUMENTS

| EP | 0900547 B1 | 3/1999 |
| GB | 2208805 A | 4/1989 |
| WO | WO 2011/019581 A1 | 2/2001 |
| WO | WO 2006/091597 A1 | 8/2006 |

(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — Omar R Rojas

(57) ABSTRACT

An illumination probe may include a handle, an optic fiber, a tube, and an illumination source connector. The tube may include a tube distal end and a tube proximal end. The tube may include a tube aperture of the tube distal end. The tube proximal end may be disposed in the handle wherein the tube distal end extends out from a distal end of the handle. The optic fiber may include an optic fiber distal end and an optic fiber proximal end. The optic fiber may be disposed in the illumination source connector, the handle, and the tube wherein the optic fiber distal end is disposed in the tube. The tube aperture may be configured to modify a property of incident illumination light.

20 Claims, 18 Drawing Sheets

(51) Int. Cl.
*A61B 5/00* (2006.01)
*A61B 9/00* (2006.01)
*A61F 9/007* (2006.01)
*A61B 90/30* (2016.01)
*A61B 3/135* (2006.01)
*A61B 90/00* (2016.01)

(52) U.S. Cl.
CPC ...... *A61B 5/0066* (2013.01); *A61B 2090/306* (2016.02); *A61B 2090/3614* (2016.02); *A61F 9/007* (2013.01)

(56) References Cited

U.S. PATENT DOCUMENTS

| | | |
|---|---|---|
| 4,147,443 A | 4/1979 | Skobel |
| 4,687,293 A | 8/1987 | Randazzo |
| 4,744,360 A | 5/1988 | Bath |
| 4,870,952 A | 10/1989 | Martinez |
| 5,190,050 A | 3/1993 | Nitzsche |
| 5,228,852 A | 7/1993 | Goldsmith et al. |
| 5,257,988 A | 11/1993 | L'Esperance, Jr. |
| 5,322,055 A | 6/1994 | Davison et al. |
| 5,322,064 A | 6/1994 | Lundquist |
| 5,346,504 A | 9/1994 | Ortiz et al. |
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,735,842 A | 4/1998 | Kruege et al. |
| 5,855,577 A | 1/1999 | Murphy-Chutorian et al. |
| 5,873,865 A | 2/1999 | Horzewski et al. |
| 5,951,544 A | 9/1999 | Konwitz |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,330,837 B1 | 12/2001 | Charles et al. |
| 6,352,531 B1 | 3/2002 | O'Connor et al. |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sheds et al. |
| 6,551,302 B1 | 4/2003 | Rosinko et al. |
| 6,554,794 B1 | 4/2003 | Mueller et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,872,214 B2 | 3/2005 | Sonnenschein et al. |
| 6,984,230 B2 | 1/2006 | Scheller et al. |
| 7,004,957 B1 | 2/2006 | Dampney et al. |
| 7,226,444 B1 | 6/2007 | Ellman et al. |
| 7,303,533 B2 | 12/2007 | Johansen et al. |
| 7,402,158 B2 | 7/2008 | Scheller et al. |
| 7,555,327 B2 | 6/2009 | Matlock |
| 7,632,242 B2 | 12/2009 | Griffin et al. |
| 7,766,904 B2 | 10/2010 | McGowan, Sr. et al. |
| 7,935,108 B2 | 5/2011 | Baxter et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,968,277 B2 | 1/2015 | Scheller et al. |
| 8,951,245 B2 | 2/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0131399 A1 | 6/2005 | Loeb et al. |
| 2005/0154379 A1 | 7/2005 | McGowen, Sr. et al. |
| 2005/0157985 A1 | 7/2005 | McGowan, Sr. et al. |
| 2005/0234437 A1 | 10/2005 | Baxter et al. |
| 2005/0272975 A1 | 12/2005 | McWeeny et al. |
| 2005/0277874 A1 | 12/2005 | Selkee |
| 2006/0129175 A1 | 6/2006 | Griffen et al. |
| 2006/0178674 A1 | 8/2006 | McIntyre |
| 2006/0293270 A1 | 12/2006 | Adamis et al. |
| 2007/0179475 A1 | 8/2007 | Scheller |
| 2007/0185514 A1 | 8/2007 | Kirchhevel |
| 2007/0260231 A1 | 11/2007 | Rose et al. |
| 2008/0132761 A1 | 6/2008 | Sonnenschein et al. |
| 2008/0208105 A1 | 8/2008 | Zelickson et al. |
| 2008/0287938 A1 | 11/2008 | Scheller |
| 2009/0018993 A1 | 1/2009 | Dick et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0191224 A1 | 7/2010 | Butcher |
| 2010/0268234 A1 | 10/2010 | Aho et al. |
| 2010/0331883 A1 | 12/2010 | Schmitz et al. |
| 2011/0028947 A1 | 2/2011 | Scheller et al. |
| 2011/0144627 A1 | 6/2011 | Smith |
| 2011/0144630 A1 | 6/2011 | Loeb |
| 2011/0190749 A1 | 8/2011 | McMillian et al. |
| 2011/0280653 A1 | 11/2011 | Sjostedt |
| 2012/0116361 A1 | 5/2012 | Hanlon et al. |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 | 4/2013 | Mansour |
| 2013/0096541 A1 | 4/2013 | Scheller et al. |
| 2013/0116671 A1 | 5/2013 | Scheller et al. |
| 2013/0144278 A1 | 6/2013 | Papac et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1 | 2/2015 | Scheller et al. |
| 2016/0302878 A1 | 10/2016 | Kern |
| 2017/0135859 A1 | 5/2017 | Scheller |
| 2018/0000645 A1* | 1/2018 | Scheller ............... G02B 6/4243 |

FOREIGN PATENT DOCUMENTS

| | | |
|---|---|---|
| WO | WO 2007/038433 A2 | 4/2007 |
| WO | WO 2013/133717 | 9/2013 |

OTHER PUBLICATIONS

Ferry P.M. Melchels, Jan Feijen, Dirk W. Grijpma, A review on stereolithography and its applications in biomedical engineering, Biomaterials 31 (2010) 6121-6130.

* cited by examiner

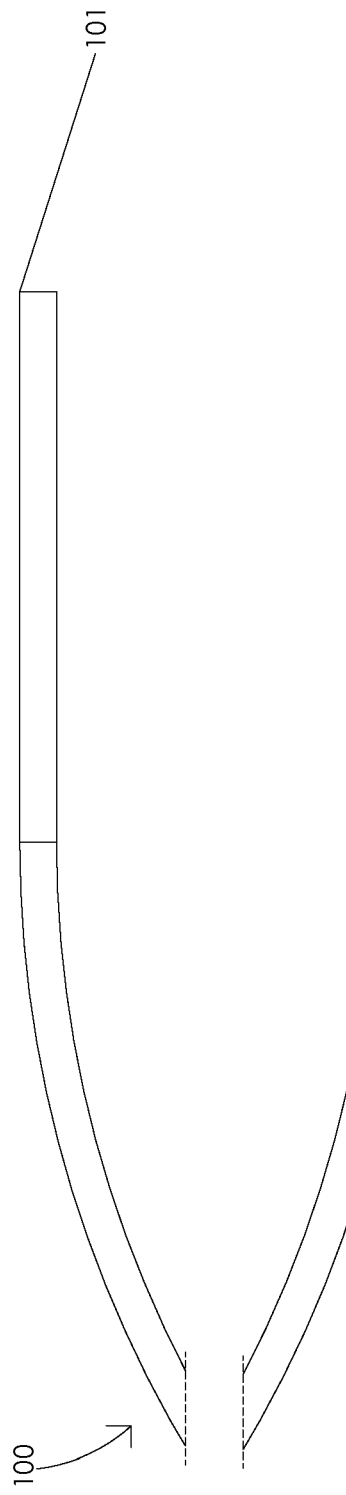
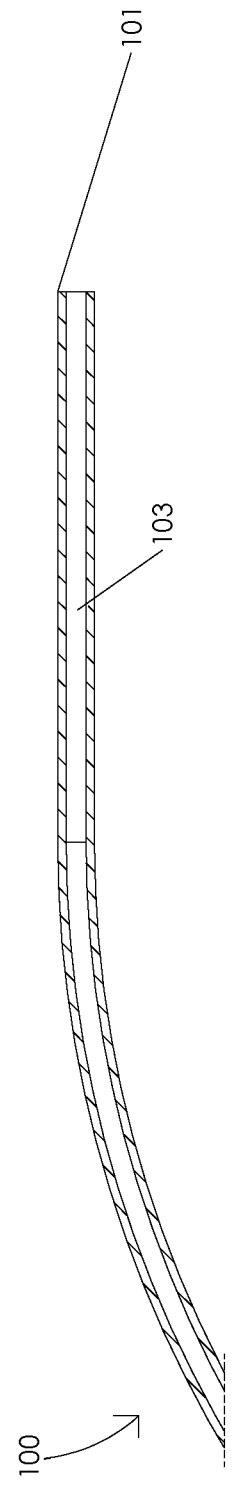
FIG. 1A
FIG. 1B

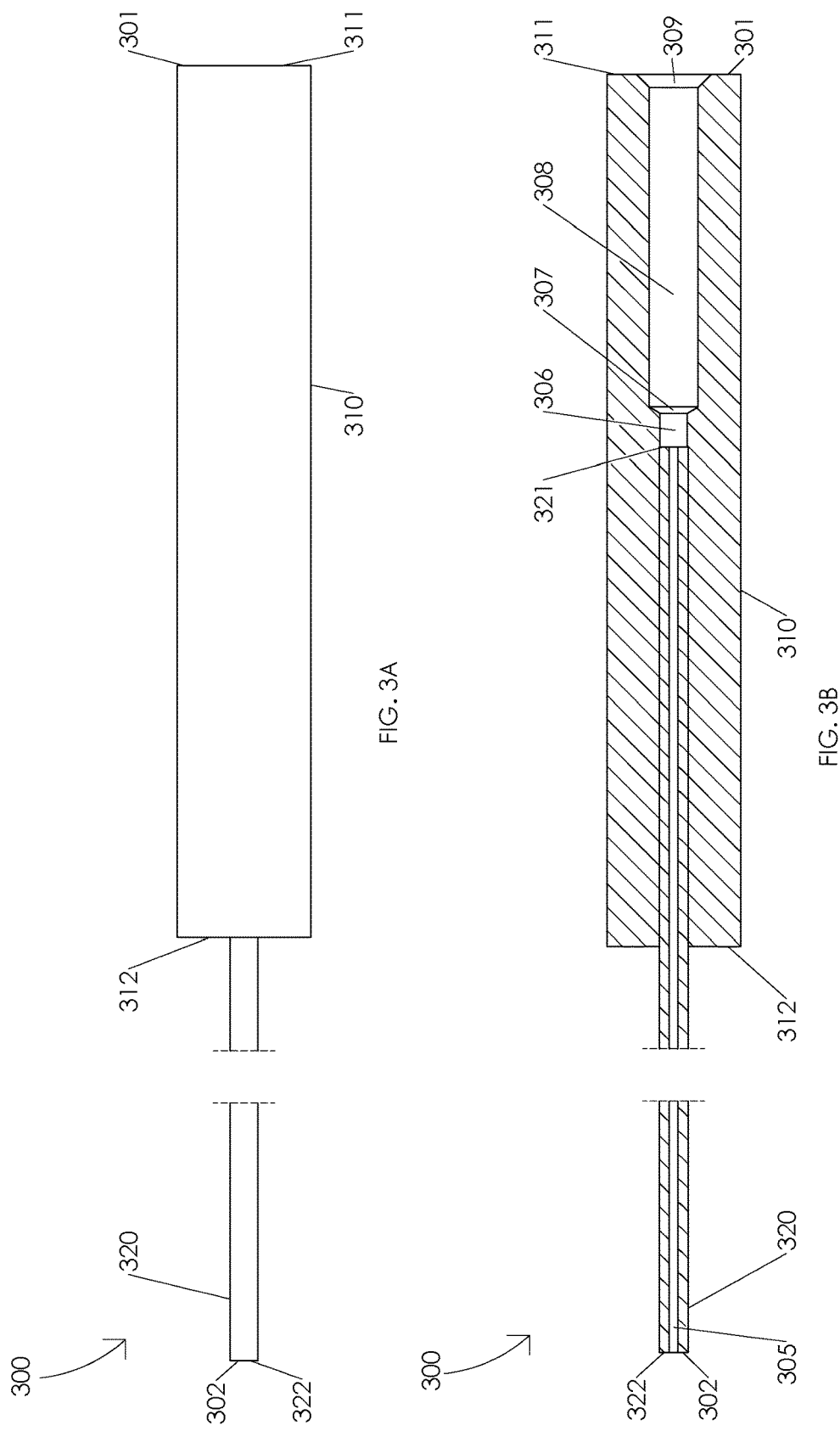

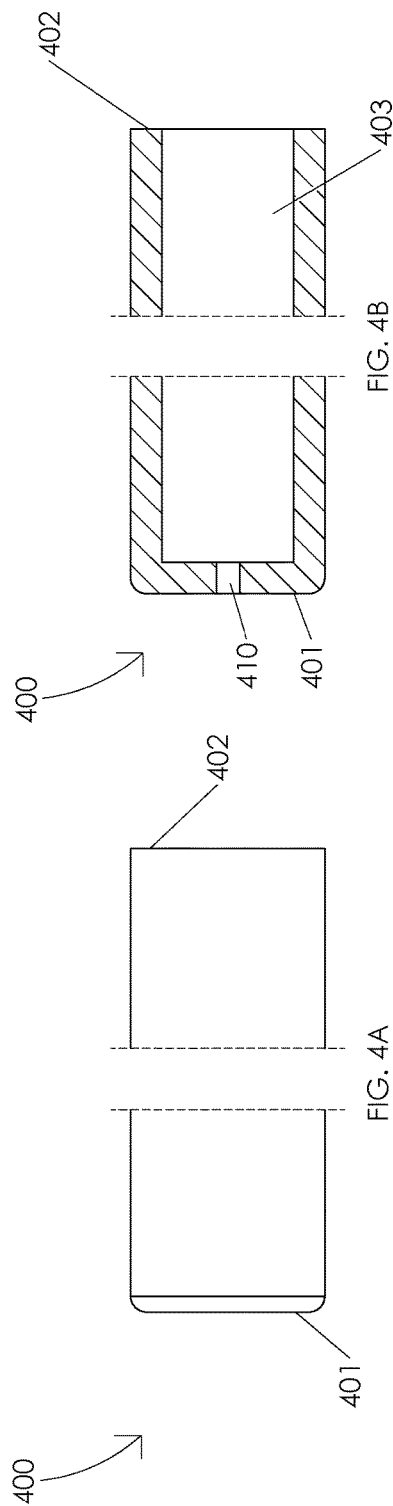

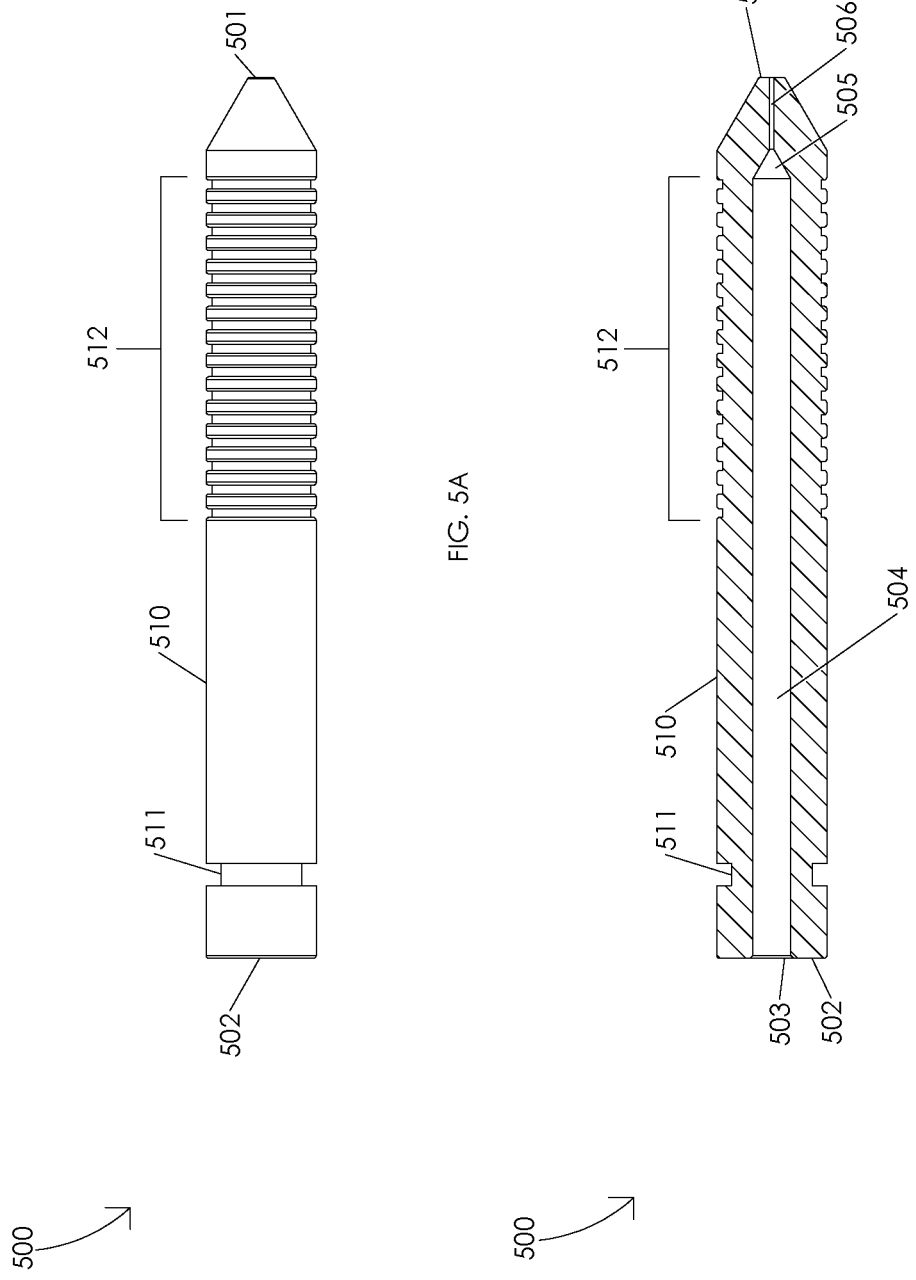

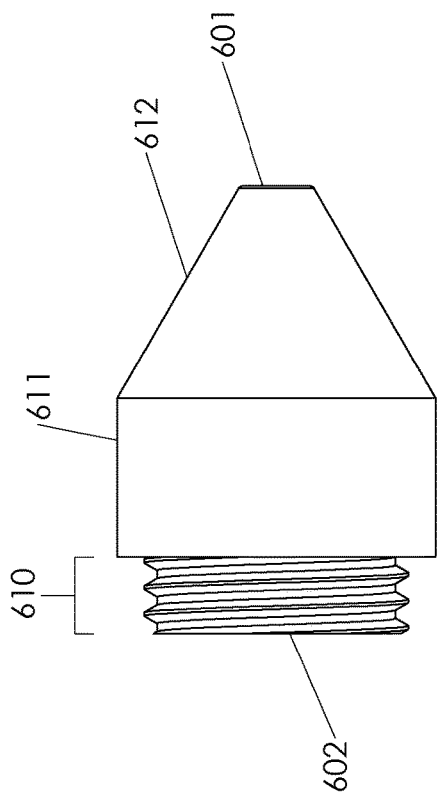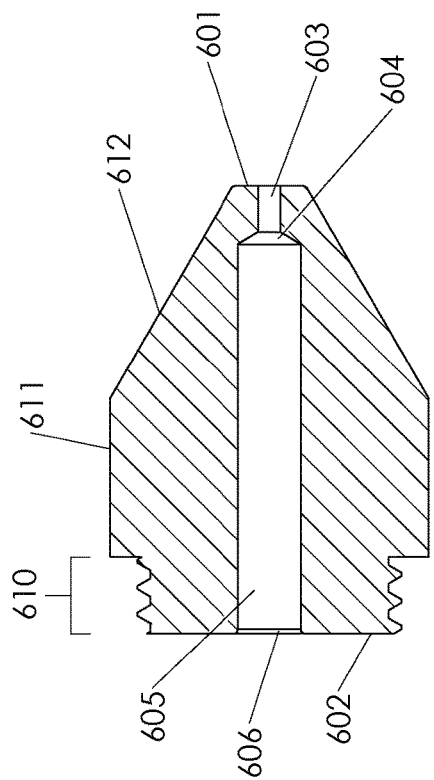

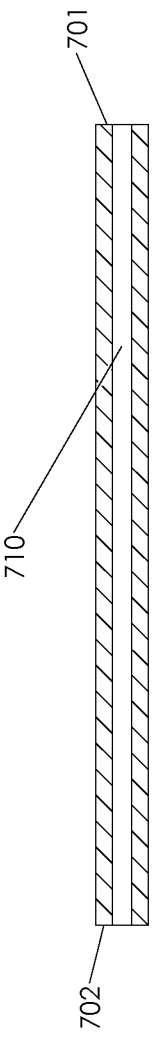

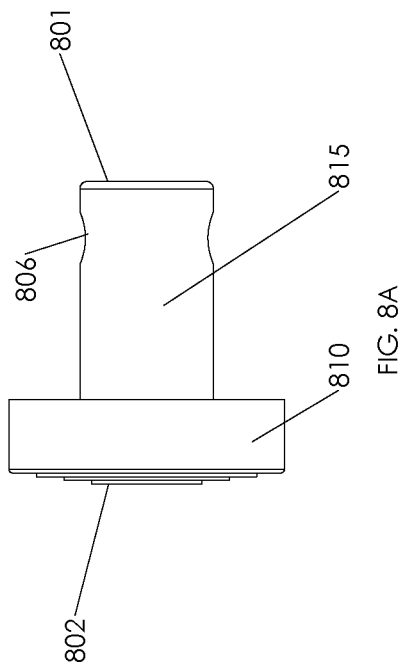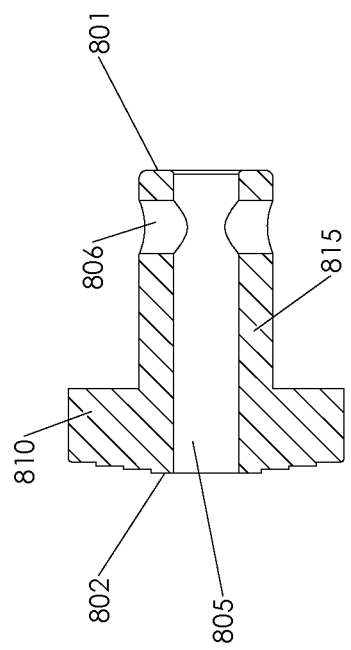

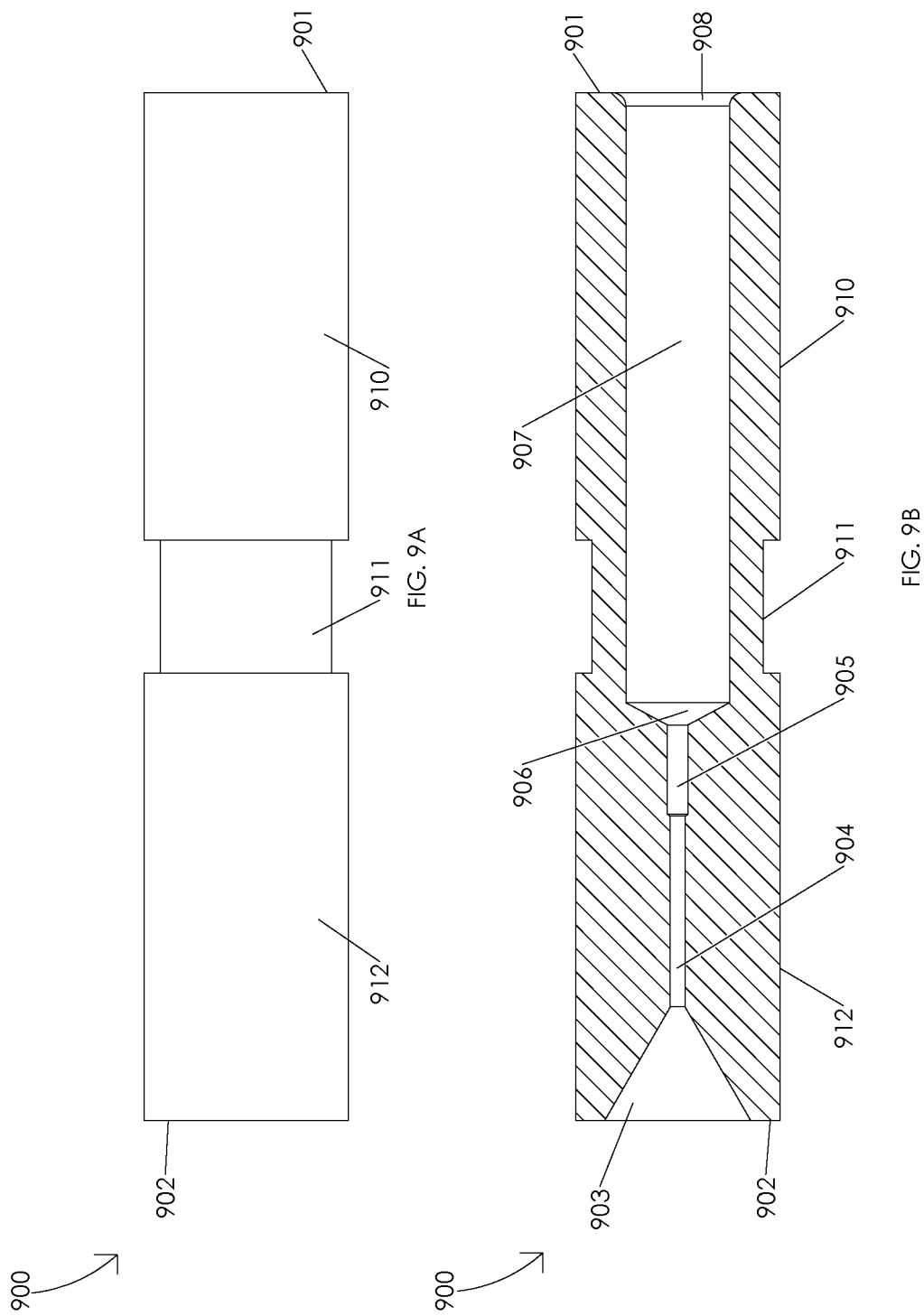

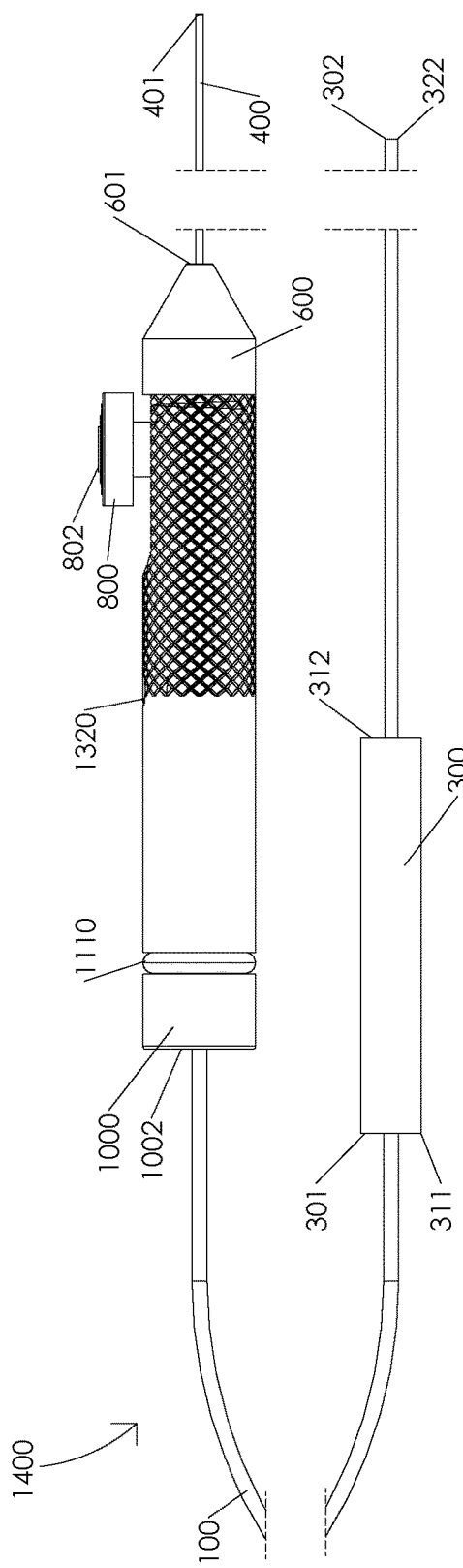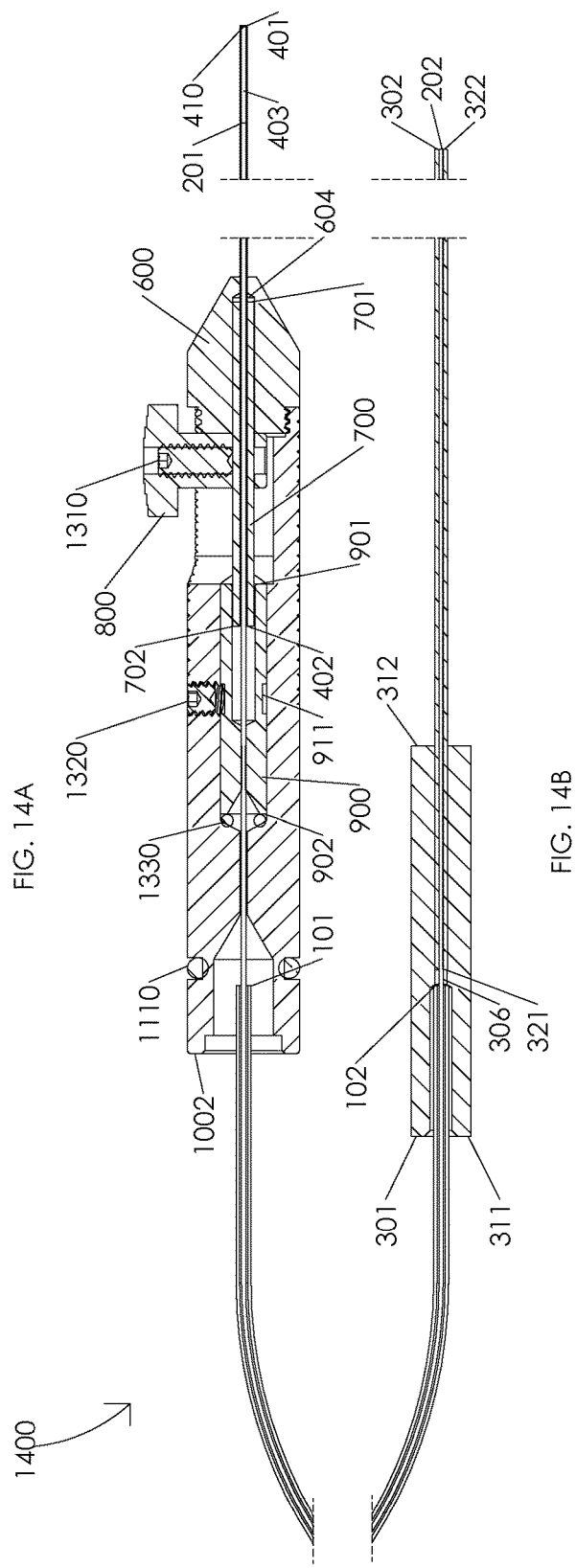
FIG. 14A
FIG. 14B

ILLUMINATION PROBE

CROSS-REFERENCE TO RELATED APPLICATIONS

This Application claims the benefit of U.S. Provisional Application No. 62/385,753, filed Sep. 9, 2016.

FIELD OF THE INVENTION

The present disclosure relates to a medical device, and, more particularly, to an illumination probe.

BACKGROUND OF THE INVENTION

Optometrists and Ophthalmologists use a slit lamp to view portions of an eye by illuminating a portion of an eye through a patient's natural or artificial lens. These procedures are not surgically invasive. Ophthalmic surgeons use external illumination sources to view portions of a patient's inner eye during surgical procedures. Surgically invasive illumination of a portion of a patient's inner eye is viewed by a surgeon through a patient's natural or artificial lens.

BRIEF SUMMARY OF THE INVENTION

The present disclosure provides an illumination probe. Illustratively, an illumination probe may comprise a handle, an optic fiber, a tube, and an illumination source connector. In one or more embodiments, the tube may comprise a tube distal end and a tube proximal end. Illustratively, the tube may comprise a tube aperture of the tube distal end. In one or more embodiments, the tube proximal end may be disposed in the handle wherein the tube distal end extends out from a distal end of the handle. Illustratively, the optic fiber may comprise an optic fiber distal end and an optic fiber proximal end. In one or more embodiments, the optic fiber may be disposed in the illumination source connector, the handle, and the tube wherein the optic fiber distal end is disposed in the tube. Illustratively, the tube aperture may be configured to modify a property of incident illumination light.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a jacketing;

FIGS. 3A and 3B are schematic diagrams illustrating an illumination source connector;

FIGS. 4A, 4B, and 4C are schematic diagrams illustrating a tube;

FIGS. 5A and 5B are schematic diagrams illustrating a handle;

FIGS. 6A and 6B are schematic diagrams illustrating a nosecone;

FIGS. 7A and 7B are schematic diagrams illustrating a piston tube;

FIGS. 8A and 8B are schematic diagrams illustrating a control mechanism;

FIGS. 9A and 9B are schematic diagrams illustrating a piston tube guide;

FIGS. 14A, 14B, 14C, and 14D are schematic diagrams illustrating an assembled adjustable illumination probe;

DETAILED DESCRIPTION OF AN ILLUSTRATIVE EMBODIMENT

FIGS. 1A and 1B are schematic diagrams illustrating a jacketing 100. FIG. 1A illustrates a side view of a jacketing 100. FIG. 1B illustrates a cross-sectional view in a sagittal plane of a jacketing 100. Illustratively, jacketing 100 may comprise a jacketing distal end 101 and a jacketing proximal end 102. In one or more embodiments, jacketing 100 may comprise a jacketing inner diameter 103. Illustratively, jacketing 100 may be manufactured from any suitable material, e.g., polymers, metals, metal alloys, etc., or from any combination of suitable materials.

Figure 2:
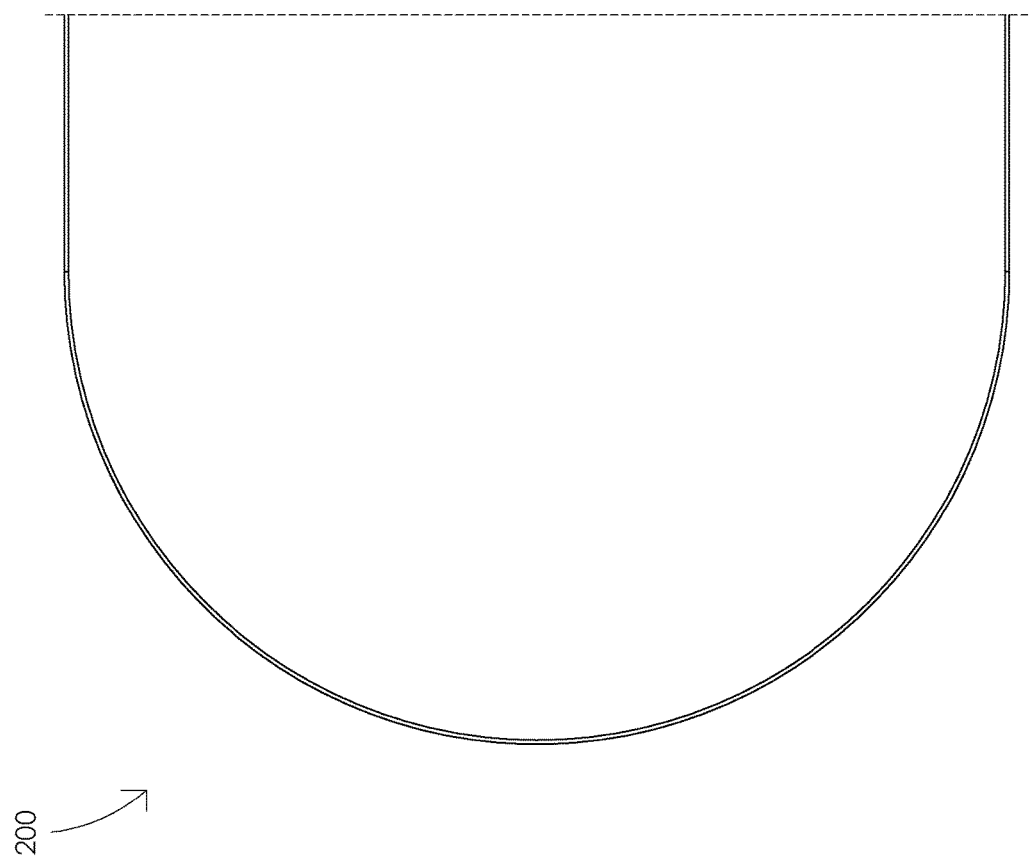
FIG. 2 is a schematic diagram illustrating an optic fiber.

FIG. 2 is a schematic diagram illustrating an optic fiber 200. In one or more embodiments, optic fiber 200 may comprise an optic fiber distal end 201 and an optic fiber proximal end 202. Illustratively, optic fiber 200 may be configured to transmit light from a surgical illumination source, e.g., light from a surgical illumination source may ingress optic fiber 200 at optic fiber proximal end 202 and light from a surgical illumination source may egress optic fiber 200 at optic fiber distal end 201. In one or more embodiments, optic fiber 200 may comprise a single optic fiber. Illustratively, optic fiber 200 may comprise a plurality of optic fibers. In one or more embodiments, optic fiber 200 may comprise one or more optic fibers manufactured from silica. Illustratively, optic fiber 200 may comprise one or more optic fibers manufactured from plastic, e.g., optic fiber 200 may comprise one or more optic fibers manufactured from Polymethyl Methacrylate Resin, Polystyrene, etc. In one or more embodiments, optic fiber 200 may comprise one or more optic fibers having a cladding material, e.g., optic fiber 200 may comprise one or more optic fibers having a cladding material manufactured from a fluorinated polymer, a silicone resin, etc. Illustratively, optic fiber 200 may comprise one or more optic fibers having a step index refractive index profile. In one or more embodiments, optic fiber 200 may comprise one or more multi-mode optic fibers, one or more single-mode optic fibers, etc. In one or more embodiments, optic fiber 200 may comprise one or more optic fibers having a core refractive index in a range of 1.3 to 1.8, e.g., optic fiber 200 may comprise one or more optic fibers having a core refractive index of 1.49. Illustratively, optic fiber 200 may comprise one or more optic fibers having a core refractive index of less than 1.3 or greater than 1.8. In one or more embodiments, optic fiber 200 may comprise one or more optic fibers having a numerical aperture in a range of 0.3 to 0.8, e.g., optic fiber 200 may comprise one or more optic fibers having a numerical aperture of 0.5. In one or more embodiments, optic fiber 200 may comprise one or more optic fibers having a numerical aperture of less than 0.3 or greater than 0.8. Illustratively, optic fiber 200 may be configured to transmit light from an illumination source having a focal spot diameter in a range of 20.0 to 60.0 micrometers, e.g., optic fiber 200 may be configured to transmit light from an illumination source having a focal spot diameter of 40.0 micrometers. In one or more embodiments, optic fiber 200 may be configured to transmit light from an illumination source having a focal spot diameter of less than 20.0 micrometers or greater than 60.0 micrometers. Illustratively, optic fiber 200 may have an outer diameter in a range of 50.0 to 750.0 micrometers, e.g., optic fiber 200 may have an outer diameter of 100.0 micrometers. In one or more embodiments, optic fiber 200 may have an outer diameter of less than 50.0 micrometers or greater than 750.0 micrometers.

FIGS. 3A and 3B are schematic diagrams illustrating an illumination source connector 300. FIG. 3A illustrates a side view of an illumination source connector 300. FIG. 3B illustrates a cross-sectional view in a sagittal plane of an illumination source connector 300. Illustratively, illumination source connector 300 may comprise an illumination source connector distal end 301 and an illumination source connector proximal end 302. In one or more embodiments, illumination source connector 300 may comprise a connector base 310 and an optic fiber housing 320. Illustratively, connector base 310 may comprise a connector base distal end 311 and a connector base proximal end 312. In one or more embodiments, connector base 310 may comprise a connector base proximal inner bore 306, a connector base proximal taper 307, a connector base distal inner bore 308, and a connector base distal taper 309. Illustratively, optic fiber housing 320 may comprise an optic fiber housing distal end 321 and an optic fiber housing proximal end 322. In one or more embodiments, optic fiber housing 320 may comprise an optic fiber housing inner bore 305. Illustratively, a portion of optic fiber housing 320 may be disposed in a portion of connector base 310, e.g., optic fiber housing distal end 321 may be disposed in connector base proximal inner bore 306. In one or more embodiments, a portion of optic fiber housing 320 may be disposed in a portion of connector base 310 wherein optic fiber housing proximal end 322 extends a distance out from connector base proximal end 312. Illustratively, a portion of optic fiber housing 320 may be fixed in a portion of connector base 310, e.g., a portion of optic fiber housing 320 may be fixed in a portion of connector base 310 by an interference fit, an adhesive, an epoxy, a setscrew, a tie, a magnetic field, a weld, a threading, etc. In one or more embodiments, connector base 300 may be manufactured from any suitable material, e.g., polymers, metals, metal alloys, etc., or from any combination of suitable materials.

FIGS. 4A, 4B, and 4C are schematic diagrams illustrating a tube 400. FIG. 4A illustrates a side view of a tube 400. FIG. 4B illustrates a cross-sectional view in a sagittal plane of a tube 400. FIG. 4C illustrates an end on view of a tube 400. Illustratively, tube 400 may comprise a tube distal end 401 and a tube proximal end 402. In one or more embodiments, tube 400 may comprise an optic fiber guide 403. Illustratively, tube 400 may comprise a tube aperture 410. In one or more embodiments, tube aperture 410 may comprise a tube aperture inferior end 411, a tube aperture superior end 412, a tube aperture distal end 413, and a tube aperture proximal end 414. Illustratively, tube aperture 400 may comprise a tube aperture width 420 and a tube aperture height 421. In one or more embodiments, tube aperture 410 may have a rectangular geometry, e.g., tuber aperture width 420 may be greater than tube aperture height 421. Illustratively, tube aperture 410 may have a circular geometry, e.g., tube aperture width 420 may be equal to tube aperture height 421. In one or more embodiments, tube aperture 410 may have a square geometry, e.g., tube aperture width 420 may be equal to tube aperture height 421. Illustratively, tube aperture width 420 may comprise a distance in a range of 0.00314 to 0.0320 inches, e.g., tube aperture width 420 may comprise a distance of 0.0201 inches. In one or more embodiments, tube aperture width 420 may comprise a distance of less than 0.00314 inches or greater than 0.0320 inches. In one or more embodiments, tube aperture height 421 may comprise a distance in a range of 0.00314 to 0.0320 inches, e.g., tube aperture height 421 may comprise a distance of 0.00708 inches. Illustratively, tube aperture height 421 may comprise a distance of less than 0.00314 inches or greater than 0.0320 inches. In one or more embodiments, tube aperture 410 may be configured to focus illumination light, e.g., tube aperture 410 may comprise a lens configured to focus illumination light. Illustratively, tube aperture 410 may comprise a lens configured to converge illumination light on an ophthalmic tissue. In one or more embodiments, tube aperture 410 may comprise a lens configured to diverge light on an ophthalmic tissue. Illustratively, tube aperture 410 may comprise a biconvex lens, a biconcave lens, a plano-convex lens, a plano-concave lens, a positive meniscus lens, a negative meniscus lens, etc. In one or more embodiments, tube aperture 410 may be configured to modify one or more properties of incident illumination light, e.g., tube aperture 410 may comprise an optical filter configured to block a particular wavelength of illumination light. Illustratively, tube aperture 410 may comprise an absorptive filter. In one or more embodiments, tube aperture 410 may comprise a dichroic filter. Illustratively, tube aperture 410 may comprise a heatsink configured to transfer heat from incident illumination light to an intraocular fluid. In one or more embodiments, tube 400 may comprise a tube face superior length 422, a tube face inferior length 423, a tube face proximal length 424, and a tube face distal length 425. Illustratively, tube 400 may be manufactured from any suitable material, e.g., polymers, metals, metal alloys, etc., or from any combination of suitable materials.

FIGS. 5A and 5B are schematic diagrams illustrating a handle 500. FIG. 5A illustrates a side view of a handle 500. FIG. 5B illustrates a cross-sectional view in a sagittal plane of a handle 500. Illustratively, handle 500 may comprise a handle distal end 501 and a handle proximal end 502. In one or more embodiments, handle 500 may comprise a handle proximal taper 503, a handle inner bore 504, a handle distal taper 505, and a tube housing 506. Illustratively, handle 500 may comprise a handle base 510, an identification ring housing 511, and a handle grip 512. In one or more embodiments, handle 500 may be manufactured from any suitable material, e.g., polymers, metals, metal alloys, etc., or from any combination of suitable materials.

FIGS. 6A and 6B are schematic diagrams illustrating a nosecone 600. FIG. 6A illustrates a side view of a nosecone 600. FIG. 6B illustrates a cross-sectional view in a sagittal plane of a nosecone 600. Illustratively, nosecone 600 may comprise a nosecone distal end 601 and a nosecone proximal end 602. In one or more embodiments, nosecone 600 may comprise a tube guide 603, a nosecone distal taper 604, a nosecone inner bore 605, and a nosecone proximal taper 606. Illustratively, nosecone 600 may comprise a nosecone threading 610, a nosecone base 611, and a nosecone outer taper 612. In one or more embodiments, nosecone 600 may be manufactured from any suitable material, e.g., polymers, metals, metal alloys, etc., or from any combination of suitable materials.

FIGS. 7A and 7B are schematic diagrams illustrating a piston tube 700. FIG. 7A illustrates a side view of a piston tube 700. FIG. 7B illustrates a cross-sectional view in a sagittal plane of a piston tube 700. Illustratively, piston tube 700 may comprise a piston tube distal end 701 and a piston tube proximal end 702. In one or more embodiments, piston tube 700 may comprise a piston tube lumen 710. Illustratively, piston tube 700 may be manufactured from any suitable material, e.g., polymers, metals, metal alloys, etc., or from any combination of suitable materials.

FIGS. 8A and 8B are schematic diagrams illustrating a control mechanism 800. FIG. 8A illustrates a side view of a control mechanism 800. FIG. 8B illustrates a cross-sectional view in a sagittal plane of a control mechanism 800. Illustratively, control mechanism 800 may comprise a control mechanism distal end 801 and a control mechanism proximal end 802. In one or more embodiments, control mechanism 800 may comprise a first fixation mechanism housing 805 and a piston tube housing 806. Illustratively, control mechanism 800 may comprise a control mechanism flange 810 and a control mechanism base 815. In one or more embodiments, control mechanism 800 may be manufactured from any suitable material, e.g., polymers, metals, metal alloys, etc., or from any combination of suitable materials.

FIGS. 9A and 9B are schematic diagrams illustrating a piston tube guide 900. FIG. 9A illustrates a side view of a piston tube guide 900. FIG. 9B illustrates a cross-sectional view in a sagittal plane of a piston tube guide 900. Illustratively, piston tube guide 900 may comprise a piston tube guide distal end 901 and a piston tube guide proximal end 902. In one or more embodiments, piston tube guide 900 may comprise a piston tube guide proximal taper 903, a piston tube guide proximal lumen 904, a piston tube guide medial lumen 905, a piston tube guide medial taper 906, a piston tube guide distal lumen 907, and a piston tube guide distal taper 908. Illustratively, piston tube guide 900 may comprise a piston tube guide distal base 910, a piston tube guide medial base 911, and a piston tube guide proximal base 912. In one or more embodiments, piston tube guide 900 may be manufactured from any suitable material, e.g., polymers, metals, metal alloys, etc., or from any combination of suitable materials.

Figure 10A:
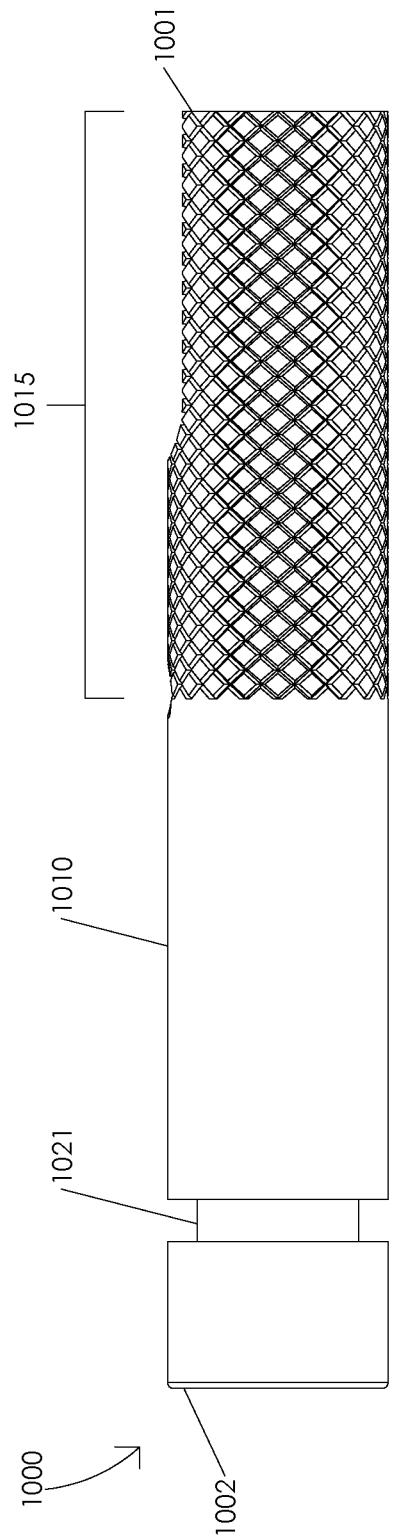
FIGS. 10A and 10B are schematic diagrams illustrating an adjustable handle.
Figure 10B:
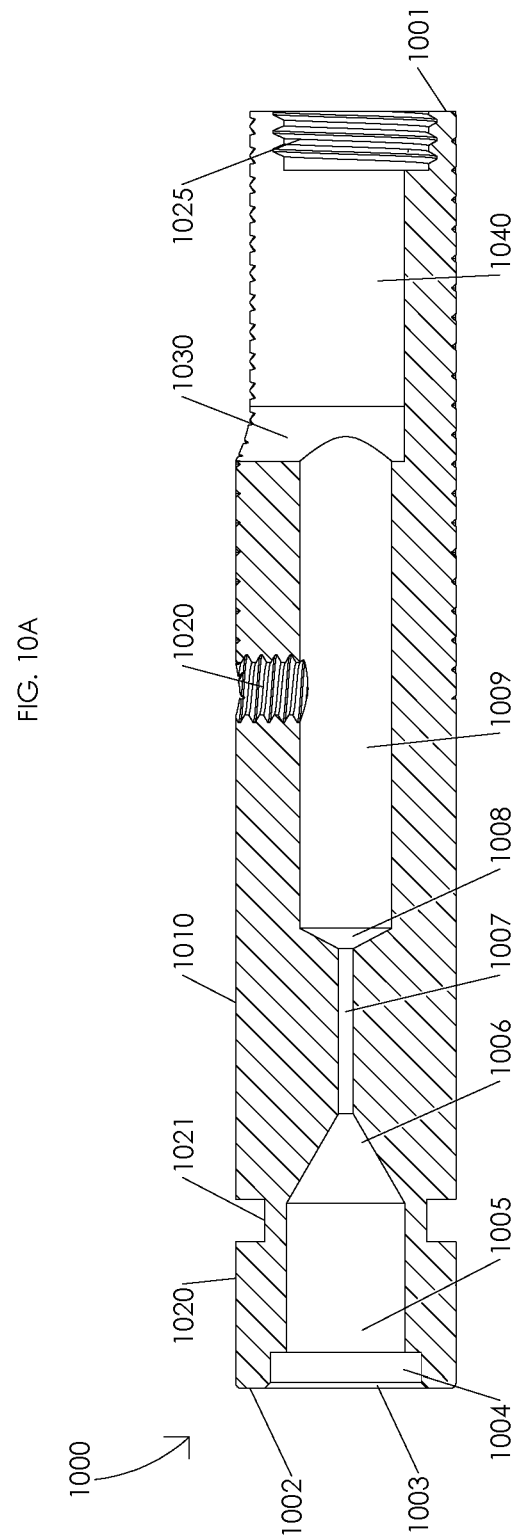

FIGS. 10A and 10B are schematic diagrams illustrating an adjustable handle 1000. FIG. 10A illustrates a side view of an adjustable handle 1000. FIG. 10B illustrates a cross-sectional view in a sagittal plane of an adjustable handle 1000. Illustratively, adjustable handle 1000 may comprise an adjustable handle distal end 1001 and an adjustable handle proximal end 1002. In one or more embodiments, adjustable handle 1000 may comprise an adjustable handle proximal taper 1003, an adjustable handle proximal chamber 1004, an adjustable handle medial chamber 1005, an adjustable handle medial taper 1006, an adjustable handle distal chamber 1007, an adjustable handle distal taper 1008, and a piston tube guide housing 1009. Illustratively, adjustable handle 1000 may comprise an adjustable handle base 1010, an adjustable handle grip 1015, a second fixation mechanism housing 1020, and an identification ring housing 1021. In one or more embodiments, adjustable handle 1000 may comprise an adjustable handle threading 1025, a control mechanism base proximal interface 1030, and a control mechanism housing 1040. Illustratively, adjustable handle 1000 may be manufactured from any suitable material, e.g., polymers, metals, metal alloys, etc., or from any combination of suitable materials.

Figure 11:
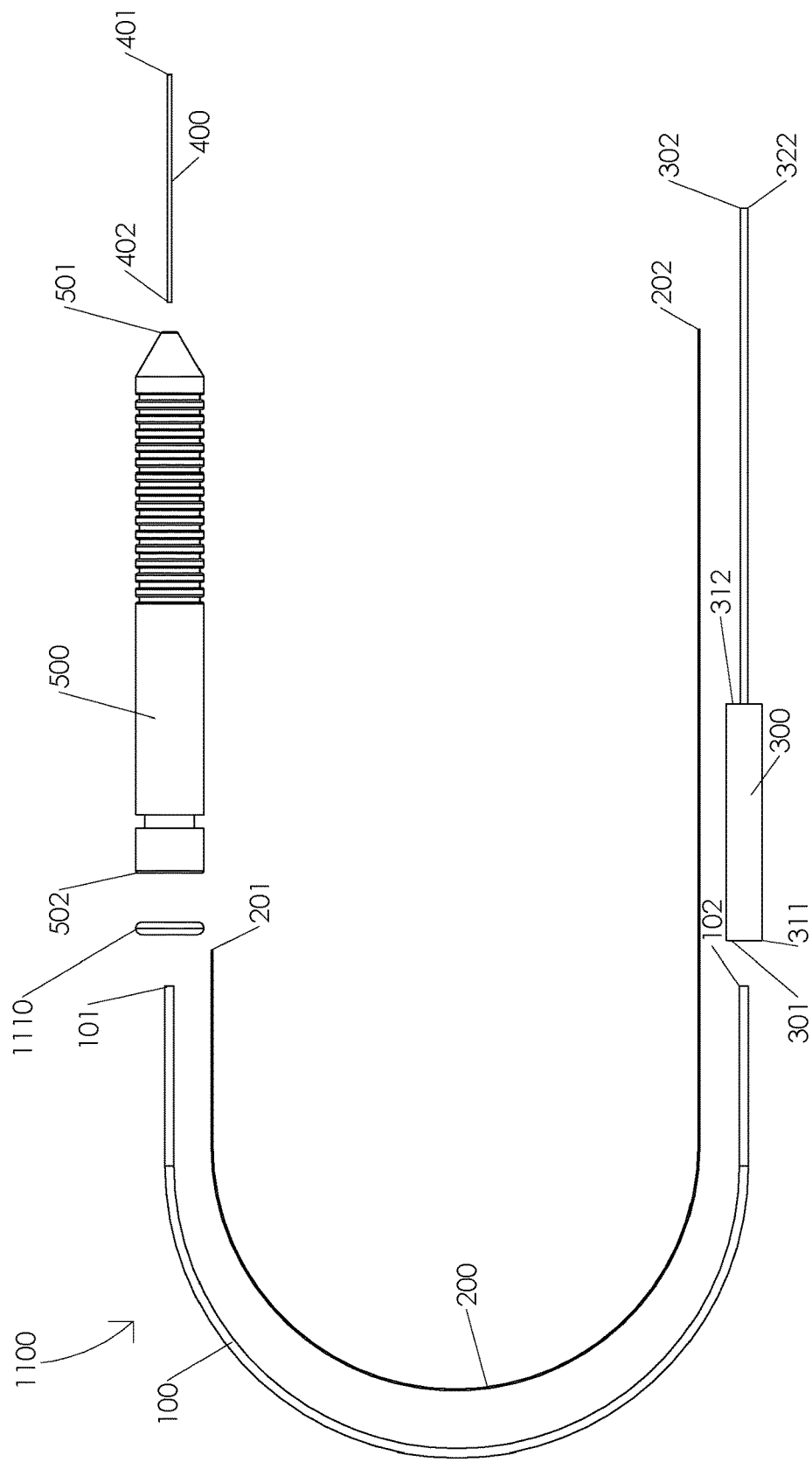
FIG. 11 is a schematic diagram illustrating an exploded view of an illumination probe assembly.

FIG. 11 is a schematic diagram illustrating an exploded view of an illumination probe assembly 1100. Illustratively, an illumination probe assembly 1100 may comprise a jacketing 100, an optic fiber 200, an illumination source connector 300, a tube 400, a handle 500, and an identification ring 1110. In one or more embodiments, identification ring 1110 may be configured to indicate one or more properties of tube 400, e.g., identification ring 1110 may be configured to visually indicate one or more properties of tube 400 to a user.

Figures 12A, 12B:
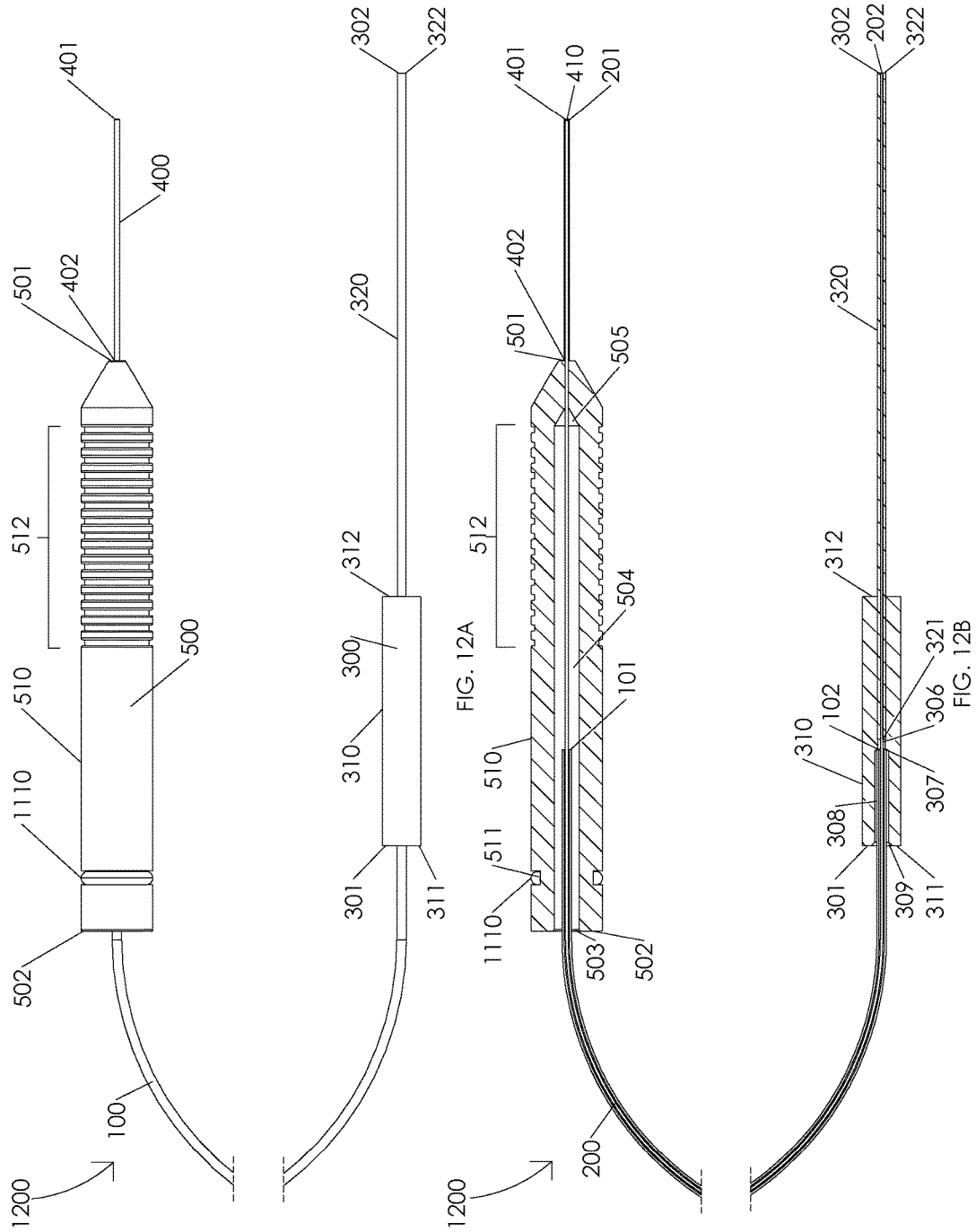
FIGS. 12A and 12B are schematic diagrams illustrating an assembled illumination probe.

FIGS. 12A and 12B are schematic diagrams illustrating an assembled illumination probe 1200. FIG. 12A illustrates a side view of an assembled illumination probe 1200. FIG. 12B illustrates a cross-sectional view in a sagittal plane of an assembled illumination probe 1200. In one or more embodiments, a portion of optic fiber 200 may be disposed in jacketing 100, e.g., a portion of optic fiber 200 may be disposed in jacketing inner diameter 103. Illustratively, optic fiber 200 may be disposed in jacketing 100 wherein optic fiber distal end 201 extends out from jacketing distal end 101. In one or more embodiments, optic fiber 200 may be disposed in jacketing 100 wherein optic fiber proximal end 202 extends out from jacketing proximal end 102. Illustratively, a portion of optic fiber 200 may be fixed in a portion of jacketing 100, e.g., a portion of optic fiber 200 may be fixed in a portion of jacketing 100 by an interference fit, an adhesive, an epoxy, a setscrew, a crimp, etc. In one or more embodiments, a portion of jacketing 100 may be disposed in a portion of illumination source connector 300, e.g., jacketing proximal end 102 may be disposed in connector base distal inner bore 308. Illustratively, a portion of jacketing 100 may be fixed in a portion of illumination source connector 300, e.g., a portion of jacketing 100 may be fixed in a portion of illumination source connector 300 by an interference fit, an adhesive, an epoxy, a setscrew, a tie, a crimp, a weld, etc. In one or more embodiments, a portion of optic fiber 200 may be disposed in illumination source connector 300, e.g., optic fiber proximal end 202 may be disposed in illumination source connector 300. Illustratively, optic fiber 200 may be disposed in connector base distal taper 309, connector base distal inner bore 308, connector base proximal taper 307, connector base proximal inner bore 306, and optic fiber housing inner bore 305. In one or more embodiments, optic fiber 200 may be disposed in illumination source connector 300 wherein optic fiber proximal end 202 is adjacent to illumination source connector proximal end 302, e.g., optic fiber 200 may be disposed in illumination source connector 300 wherein optic fiber proximal end 202 is adjacent to optic fiber housing proximal end 322. Illustratively, optic fiber 200 may be disposed in illumination source connector 300 wherein optic fiber proximal end 202 abuts illumination source connector proximal end 302, e.g., optic fiber 200 may be disposed in illumination source connector 300 wherein optic fiber proximal end 202 abuts optic fiber housing proximal end 322. In one or more embodiments, optic fiber 200 may be disposed in illumination source connector 300 wherein optic fiber proximal end 202 is coplanar with illumination source connector proximal end 302, e.g., optic fiber 200 may be disposed in illumination source connector 300 wherein optic fiber proximal end 202 is coplanar with optic fiber housing proximal end 322. Illustratively, a portion of optic fiber 200 may be fixed in a portion of illumination source connector 300, e.g., a portion of optic fiber 200 may be fixed in a portion of illumination source connector 300 by an interference fit, an adhesive, an epoxy, a setscrew, a crimp, etc.

In one or more embodiments, a portion of tube 400 may be disposed in a portion of handle 500, e.g., tube proximal end 402 may be disposed in tube housing 506. Illustratively, a portion of tube 400 may be disposed in a portion of handle 500 wherein tube distal end 401 extends out from handle distal end 501. In one or more embodiments, a portion of tube 400 may be fixed in a portion of handle 500, e.g., a portion of tube 400 may be fixed in a portion of handle 500 by an interference fit, an adhesive, an epoxy, a setscrew, a tie, a crimp, a weld, a threading, etc. Illustratively, identification ring 1110 may be disposed in identification ring housing 511. In one or more embodiments, identification ring 1110 may be fixed in identification ring housing 511, e.g., identification ring 1110 may be fixed in identification ring housing 511 by a force of friction, an adhesive, and epoxy, etc. Illustratively, a portion of jacketing 100 may be disposed in a portion of handle 500, e.g., jacketing distal end 101 may be disposed in handle inner bore 504. In one or more embodiments, a portion of jacketing 100 may be fixed in a portion of handle 500, e.g., a portion of jacketing 100 may be fixed in a portion of handle 500 by an interference fit, an adhesive, an epoxy, a setscrew, a tie, a crimp, a weld, a threading, etc.

Illustratively, a portion of optic fiber 200 may be disposed in handle 500 and tube 400. In one or more embodiments, optic fiber 200 may be disposed in handle proximal taper 503, handle inner bore 504, handle distal taper 505, tube housing 506, and optic fiber guide 403. Illustratively, optic fiber 200 may be disposed in tube 400 wherein optic fiber distal end 201 is adjacent to tube distal end 401, e.g., optic fiber 200 may be disposed in tube 400 wherein optic fiber distal end 201 abuts tube distal end 401. In one or more embodiments, optic fiber 200 may be disposed in tube 400 wherein optic fiber distal end 201 is coplanar with tube distal end 401, e.g., optic fiber 200 may be disposed in tube 400 wherein optic fiber distal end 201 is flush with tube distal end 401. Illustratively, optic fiber 200 may be disposed in tube 400 wherein optic fiber distal end 201 is adjacent to tube aperture 410, e.g., optic fiber 200 may be disposed in tube 400 wherein optic fiber distal end 201 abuts tube aperture 410. In one or more embodiments, optic fiber 200 may be disposed in tube 400 wherein optic fiber distal end 201 is coplanar with tube aperture 410, e.g., optic fiber 200 may be disposed in tube 400 wherein optic fiber distal end 201 is flush with tube aperture 410. Illustratively, optic fiber 200 may be disposed in tube 400 wherein a portion of optic fiber 200 is disposed in tube aperture 410, e.g., optic fiber 200 may be disposed in tube 400 wherein optic fiber distal end 201 is disposed in tube aperture 410. In one or more embodiments, a portion of optic fiber 200 may be fixed in a portion of tube 400, e.g., a portion of optic fiber 200 may be fixed in a portion of tube 400 by an interference fit, an adhesive, an epoxy, a setscrew, a tie, a crimp, a weld, a threading, etc. Illustratively, a portion of optic fiber 200 may be fixed in handle 500, e.g., a portion of optic fiber 200 may be fixed in handle 500 by an interference fit, an adhesive, an epoxy, a setscrew, a tie, a crimp, a weld, a threading, etc.

Figure 13:
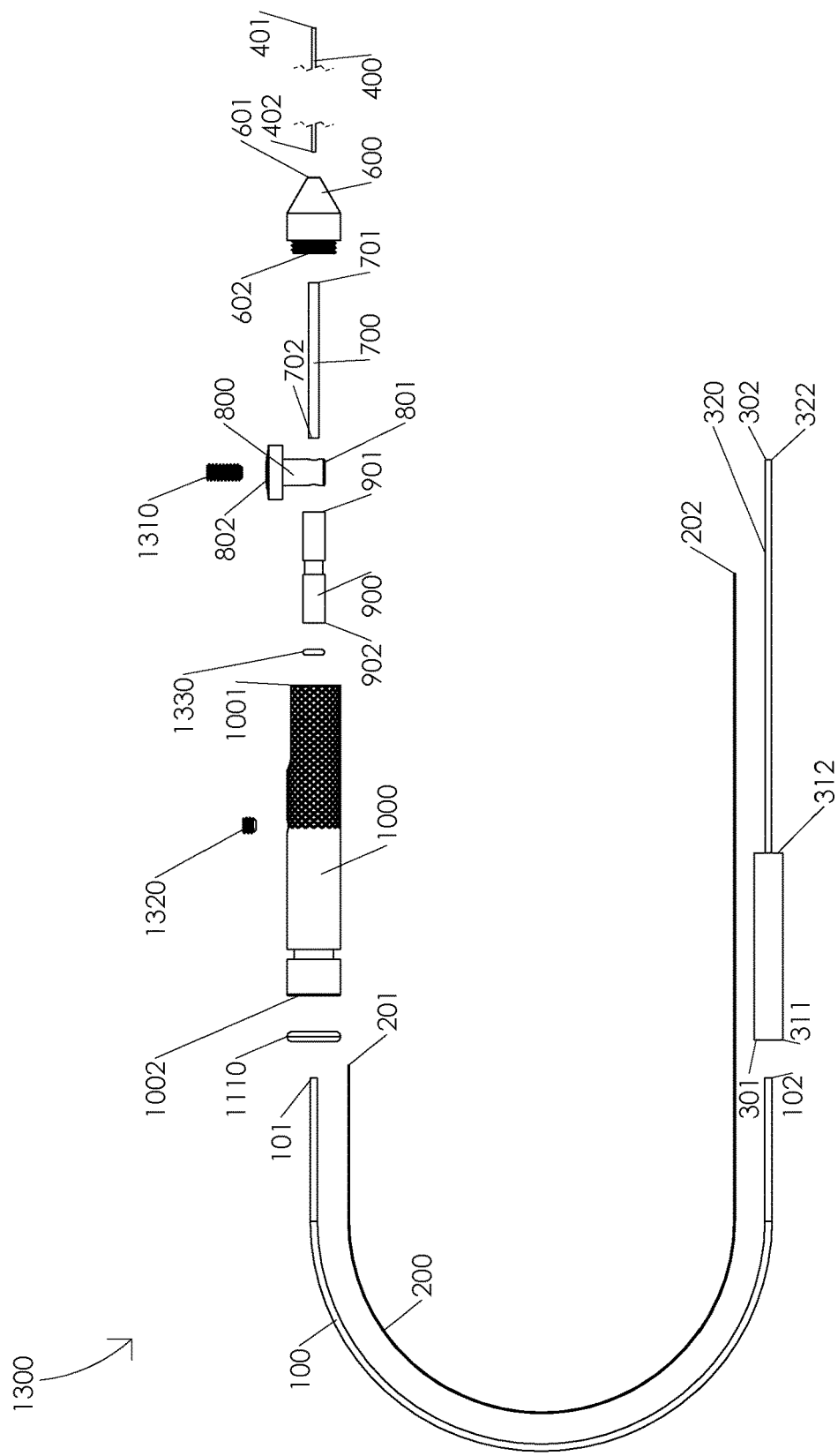
FIG. 13 is a schematic diagram illustrating an exploded view of an adjustable illumination probe assembly.

FIG. 13 is a schematic diagram illustrating an exploded view of an adjustable illumination probe assembly 1300. In one or more embodiments, an adjustable illumination probe assembly 1300 may comprise a jacketing 100, an optic fiber 200, an illumination source connector 300, a tube 400, a nosecone 600, a piston tube 700, a control mechanism 800, a piston tube guide 900, an adjustable handle 1000, an identification ring, 1110, a first fixation mechanism 1310, a second fixation mechanism 1320, and a hermetic seal ring 1330.

Figure 14C:
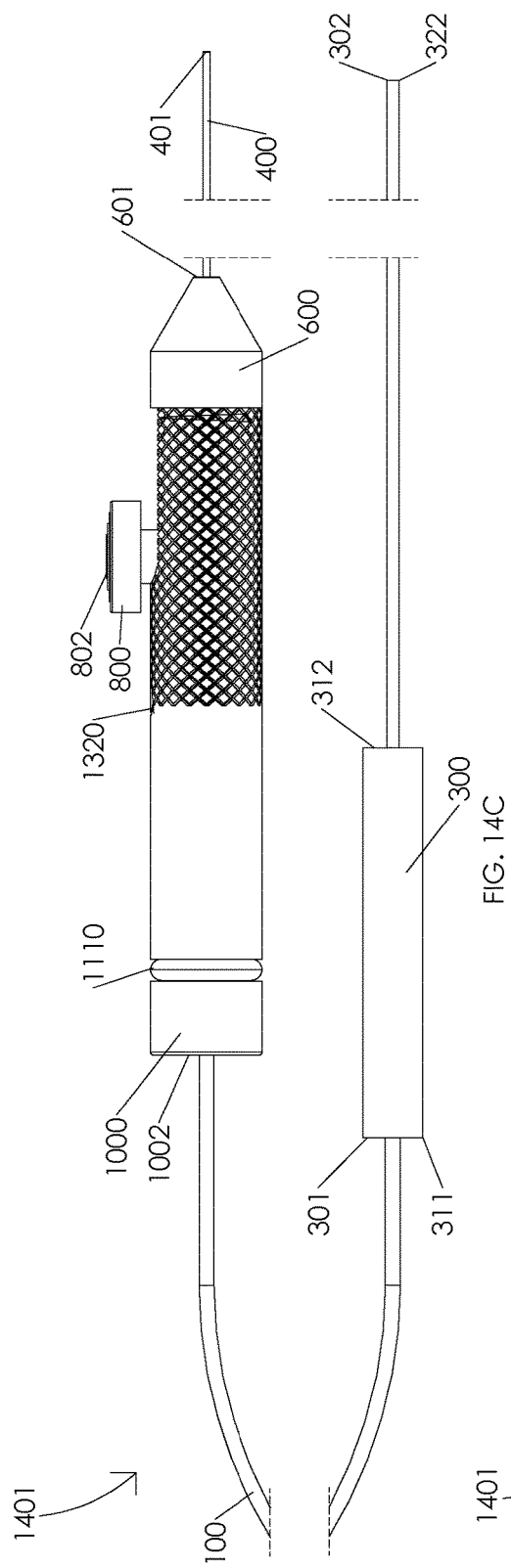
Figure 14D:
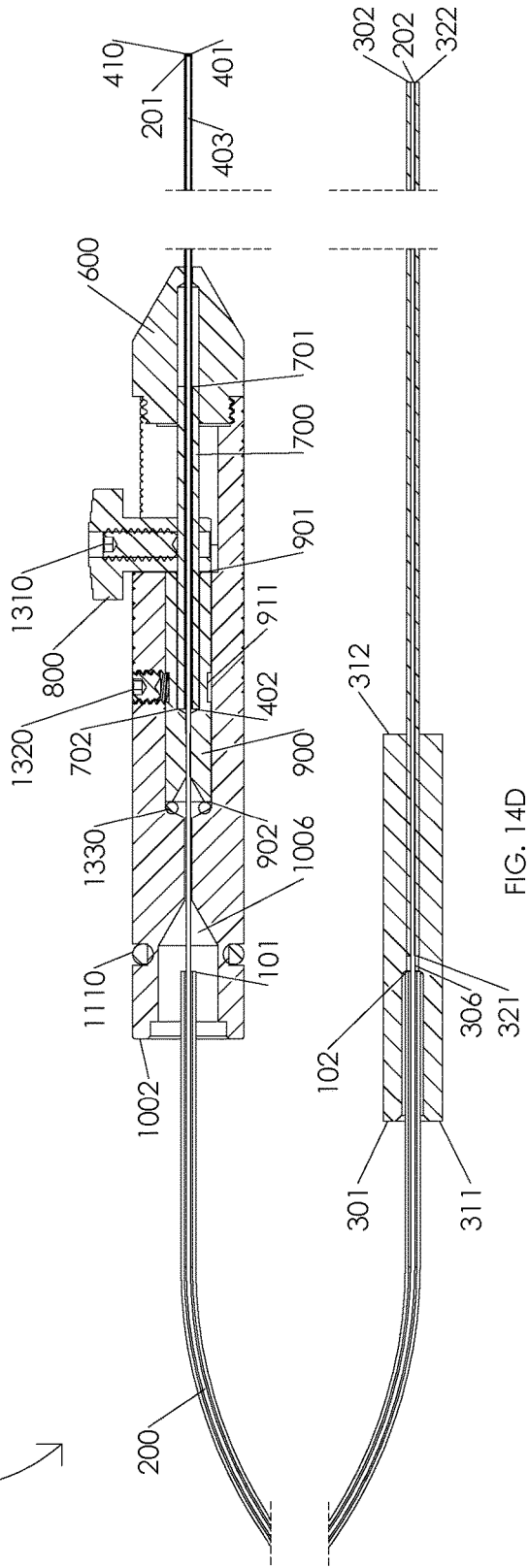

FIGS. 14A, 14B, 14C, and 14D are schematic diagrams illustrating an assembled adjustable illumination probe. FIG. 14A illustrates a side view of an assembled adjustable illumination probe with extended tube 1400. FIG. 14B illustrates a cross-sectional view in a sagittal plane of an assembled adjustable illumination probe with extended tube 1400. FIG. 14C illustrates a side view of an assembled adjustable illumination probe with retracted tube 1401. FIG. 14D illustrates a cross-sectional view in a sagittal plane of an assembled adjustable illumination probe with retracted tube 1401.

In one or more embodiments, a portion of optic fiber 200 may be disposed in jacketing 100, e.g., a portion of optic fiber 200 may be disposed in jacketing inner diameter 103. Illustratively, optic fiber 200 may be disposed in jacketing 100 wherein optic fiber distal end 201 extends out from jacketing distal end 101. In one or more embodiments, optic fiber 200 may be disposed in jacketing 100 wherein optic fiber proximal end 202 extends out from jacketing proximal end 102. Illustratively, a portion of optic fiber 200 may be fixed in a portion of jacketing 100, e.g., a portion of optic fiber 200 may be fixed in a portion of jacketing 100 by an interference fit, an adhesive, an epoxy, a setscrew, a crimp, etc. In one or more embodiments, a portion of jacketing 100 may be disposed in a portion of illumination source connector 300, e.g., jacketing proximal end 102 may be disposed in connector base distal inner bore 308. Illustratively, a portion of jacketing 100 may be fixed in a portion of illumination source connector 300, e.g., a portion of jacketing 100 may be fixed in a portion of illumination source connector 300 by an interference fit, an adhesive, an epoxy, a setscrew, a tie, a crimp, a weld, etc. In one or more embodiments, a portion of optic fiber 200 may be disposed in illumination source connector 300, e.g., optic fiber proximal end 202 may be disposed in illumination source connector 300. Illustratively, optic fiber 200 may be disposed in connector base distal taper 309, connector base distal inner bore 308, connector base proximal taper 307, connector base proximal inner bore 306, and optic fiber housing inner bore 305. In one or more embodiments, optic fiber 200 may be disposed in illumination source connector 300 wherein optic fiber proximal end 202 is adjacent to illumination source connector proximal end 302, e.g., optic fiber 200 may be disposed in illumination source connector 300 wherein optic fiber proximal end 202 is adjacent to optic fiber housing proximal end 322. Illustratively, optic fiber 200 may be disposed in illumination source connector 300 wherein optic fiber proximal end 202 abuts illumination source connector proximal end 302, e.g., optic fiber 200 may be disposed in illumination source connector 300 wherein optic fiber proximal end 202 abuts optic fiber housing proximal end 322. In one or more embodiments, optic fiber 200 may be disposed in illumination source connector 300 wherein optic fiber proximal end 202 is coplanar with illumination source connector proximal end 302, e.g., optic fiber 200 may be disposed in illumination source connector 300 wherein optic fiber proximal end 202 is coplanar with optic fiber housing proximal end 322. Illustratively, a portion of optic fiber 200 may be fixed in a portion of illumination source connector 300, e.g., a portion of optic fiber 200 may be fixed in a portion of illumination source connector 300 by an interference fit, an adhesive, an epoxy, a setscrew, a crimp, etc.

In one or more embodiments, a portion of nosecone 600 may be disposed in a portion of adjustable handle 1000, e.g., nosecone proximal end 602 may be disposed in adjustable handle 1000. Illustratively, a portion of nosecone 600 may be disposed in a portion of adjustable handle 1000 wherein nosecone distal end 601 extends out from adjustable handle distal end 1001. In one or more embodiments, a portion of nosecone 600 may be fixed in a portion of handle 1000, e.g., a portion of nosecone 600 may be fixed in a portion of handle 1000 by an interference fit, an adhesive, an epoxy, a setscrew, a tie, a crimp, a weld, a threading, etc. Illustratively, nosecone threading 610 and adjustable handle threading 1025 may be configured to fix a portion of nosecone 600 in a portion of adjustable handle 1000. In one or more embodiments, identification ring 1110 may be disposed in identification ring housing 1021. Illustratively, identification ring 1110 may be fixed in identification ring housing 1021, e.g., identification ring 1110 may be fixed in identification ring housing 1021 by a force of friction, an adhesive, and epoxy, etc.

In one or more embodiments, piston tube guide 900 may be disposed in adjustable handle 1000, e.g., piston tube guide 900 may be disposed in piston tube guide housing 1009. Illustratively, piston tube guide 900 may be disposed in piston tube guide housing 1009 wherein piston tube guide proximal end 902 is adjacent to adjustable handle distal taper 1008, e.g., piston tube guide 900 may be disposed in piston tube guide housing 1009 wherein piston tube guide proximal end 902 abuts handle distal taper 1008. In one or more embodiments, piston tube guide 900 may be disposed in piston tube guide housing 1009 wherein piston tube guide distal end 901 is adjacent to control mechanism base proximal interface 1030, e.g., piston tube guide 900 may be disposed in piston tube guide housing 1009 wherein piston tube guide distal end 901 abuts control mechanism base proximal interface 1030. Illustratively, piston tube guide 900 may be fixed in piston tube guide housing 1009, e.g., piston tube guide 900 may be fixed in piston tube guide housing 1009 by an interference fit, an adhesive, an epoxy, a setscrew, a tie, a crimp, a weld, a threading, etc. In one or more embodiments, second fixation mechanism 1320 may be configured to fix piston tube guide 900 in piston tube guide housing 1009, e.g., second fixation mechanism 1320 may be disposed in second fixation mechanism housing 1020. Illustratively, second fixation mechanism 1320 may comprise a setscrew configured to fix piston tube guide 900 in piston tube guide housing 1009.

In one or more embodiments, hermetic seal ring 1330 may be disposed in adjustable handle distal taper 1008 and piston tube guide proximal taper 903, e.g., hermetic seal ring 1330 may be configured to form a hermetic seal between adjustable handle distal taper 1008 and piston tube guide proximal taper 903. Illustratively, hermetic seal ring 1330 may be fixed in adjustable handle distal taper 1008 and piston tube guide proximal taper 903, e.g., hermetic seal ring 1330 may be fixed in adjustable handle distal taper 1008 and piston tube guide proximal taper 903 by an interference fit, an adhesive, an epoxy, a setscrew, a tie, a crimp, a weld, a threading, etc. In one or more embodiments, piston tube 700 may be disposed in piston tube guide distal lumen 907, control mechanism housing 1040, piston tube housing 806, and nosecone inner bore 605. Illustratively, piston tube 700 may be fixed in piston tube housing 806, e.g., piston tube 700 may be fixed in piston tube housing 806 by an interference fit, an adhesive, an epoxy, a setscrew, a tie, a crimp, a weld, a threading, etc. In one or more embodiments, first fixation mechanism 1310 may be configured to fix piston tube 700 in piston tube housing 806, e.g., first fixation mechanism 1310 may be disposed in first fixation mechanism housing 805. Illustratively, first fixation mechanism 1310 may comprise a setscrew configured to fix piston tube 700 in piston tube housing 806. In one or more embodiments, a portion of control mechanism 800 may be disposed in control mechanism housing 1040, e.g., control mechanism base 815 may be disposed in control mechanism housing 1040. Illustratively, a portion of control mechanism 800 may be fixed in control mechanism housing 1040, e.g., first fixation mechanism 1310 may be configured to fix a portion of control mechanism 800 in control mechanism housing 1040 by fixing piston tube 700 in piston tube housing 806. For example, a length of piston tube 700 may be configured to fix a portion of control mechanism 800 in control mechanism housing 1040. In one or more embodiments, piston tube 700 may be configured to actuate proximally and distally within piston tube guide distal lumen 907, control mechanism housing 1040, and nosecone inner bore 605. Illustratively, a portion of control mechanism 800 may be configured to actuate proximally and distally within control mechanism housing 1040. In one or more embodiments, an actuation of control mechanism 800 within control mechanism housing 1040 may be configured to actuate piston tube 700 within piston tube guide distal lumen 907, control mechanism housing 1040, and nosecone inner bore 605.

Illustratively, a portion of tube 400 may be disposed in nosecone 600 and a portion of piston tube 700, e.g., a portion of tube 400 may be disposed in tube guide 603, nosecone distal taper 604, and piston tube lumen 710. In one or more embodiments, a portion of tube 400 may be disposed in nosecone 600 and a portion of piston tube 700 wherein tube distal end 401 extends out from nosecone distal end 601. Illustratively, a portion of tube 400 may be fixed in piston tube lumen 710, e.g., a portion of tube 400 may be fixed in piston tube lumen 710 by an interference fit, an adhesive, an epoxy, a setscrew, a tie, a crimp, a weld, a threading, etc. In one or more embodiments, a portion of tube 400 may be fixed in piston tube lumen 710 wherein an actuation of piston tube 700 is configured to actuate tube 400, e.g., tube proximal end 402 may be fixed in piston tube lumen 710 wherein an actuation of piston tube 700 is configured to actuate tube 400. In one or more embodiments, a portion of jacketing 100 may be disposed in a portion of adjustable handle 1000, e.g., jacketing distal end 101 may be disposed in adjustable handle medial chamber 1005. Illustratively, a portion of jacketing 100 may be fixed in a portion of adjustable handle 1000, e.g., a portion of jacketing 100 may be fixed in a portion of adjustable handle 1000 by an interference fit, an adhesive, an epoxy, a setscrew, a tie, a crimp, a weld, a threading, etc.

In one or more embodiments, a portion of optic fiber 200 may be disposed in adjustable handle 1000, nosecone 600, and tube 400. Illustratively, optic fiber 200 may be disposed in adjustable handle proximal taper 1003, adjustable handle proximal chamber 1004, adjustable handle medial chamber 1005, adjustable handle medial taper 1006, adjustable handle distal chamber 1007, adjustable handle distal taper 1008, piston tube guide housing 1009, piston tube lumen 710, control mechanism housing 1040, control mechanism 800, nosecone proximal taper 606, nosecone inner bore 605, nosecone distal taper 604, tube guide 603, and optic fiber guide 403. In one or more embodiments, a portion of optic fiber 200 may be fixed in a position relative to adjustable handle 1000, e.g., a portion of optic fiber 200 may be fixed in adjustable handle distal chamber 1007. Illustratively, a portion of optic fiber 200 may be fixed in a position relative to adjustable handle 1000 by an interference fit, an adhesive, an epoxy, a setscrew, a tie, a crimp, a weld, a threading, etc. In one or more embodiments, an actuation of control mechanism 800 towards adjustable handle distal end 1001 and away from adjustable handle proximal end 1002 may be configured to extend piston tube 700 relative to adjustable handle 1000. Illustratively, an extension of piston tube 700 relative to adjustable handle 1000 may be configured to extend tube 400 relative to optic fiber 200. In one or more embodiments, tube 400 may be fully extended relative to optic fiber 200 when an assembled adjustable illumination probe comprises an assembled adjustable illumination probe with extended tube 1400. Illustratively, an actuation of control mechanism 800 towards adjustable handle proximal end 1002 and away from adjustable handle distal end 1001 may be configured to retract piston tube 700 relative to adjustable handle 1000. In one or more embodiments, a retraction of piston tube 700 relative to adjustable handle 1000 may be configured to retract tube 400 relative to optic fiber 200. Illustratively, tube 400 may be fully retracted relative to optic fiber 200 when an assembled adjustable illumination probe comprises an assembled adjustable illumination probe with retracted tube 1401.

Illustratively, optic fiber 200 may be disposed in tube 400 wherein optic fiber distal end 201 is not adjacent to tube distal end 401 when an assembled adjustable illumination probe comprises an assembled adjustable illumination probe with extended tube 1400, e.g., optic fiber 200 may be disposed in tube 400 wherein optic fiber distal end 201 does not abut tube distal end 401 when an assembled adjustable illumination probe comprises an assembled adjustable illumination probe with extended tube 1400. In one or more embodiments, optic fiber 200 may be disposed in tube 400 wherein optic fiber distal end 201 is not coplanar with tube distal end 401 when an assembled adjustable illumination probe comprises an assembled adjustable illumination probe with extended tube 1400, e.g., optic fiber 200 may be disposed in tube 400 wherein optic fiber distal end 201 is not flush with tube distal end 401 when an assembled adjustable illumination probe comprises an assembled adjustable illumination probe with extended tube 1400. Illustratively, optic fiber 200 may be disposed in tube 400 wherein optic fiber distal end 201 is not adjacent to tube aperture 410 when an assembled adjustable illumination probe comprises an assembled adjustable illumination probe with extended tube 1400, e.g., optic fiber 200 may be disposed in tube 400 wherein optic fiber distal end 201 does not abut tube aperture 410 when an assembled adjustable illumination probe comprises an assembled adjustable illumination probe with extended tube 1400. In one or more embodiments, optic fiber 200 may be disposed in tube 400 wherein optic fiber distal end 201 is not coplanar with tube aperture 410 when an assembled adjustable illumination probe comprises an assembled adjustable illumination probe with extended tube 1400, e.g., optic fiber 200 may be disposed in tube 400 wherein optic fiber distal end 201 is not flush with tube aperture 410 when an assembled adjustable illumination probe comprises an assembled adjustable illumination probe with extended tube 1400. Illustratively, optic fiber 200 may be disposed in tube 400 wherein a portion of optic fiber 200 is not disposed in tube aperture 410 when an assembled adjustable illumination probe comprises an assembled adjustable illumination probe with extended tube 1400, e.g., optic fiber 200 may be disposed in tube 400 wherein optic fiber distal end 201 is not disposed in tube aperture 410 when an assembled adjustable illumination probe comprises an assembled adjustable illumination probe with extended tube 1400.

Illustratively, optic fiber 200 may be disposed in tube 400 wherein optic fiber distal end 201 is adjacent to tube distal end 401 when an assembled adjustable illumination probe comprises an assembled adjustable illumination probe with retracted tube 1401, e.g., optic fiber 200 may be disposed in tube 400 wherein optic fiber distal end 201 abuts tube distal end 401 when an assembled adjustable illumination probe comprises an assembled adjustable illumination probe with retracted tube 1401. In one or more embodiments, optic fiber 200 may be disposed in tube 400 wherein optic fiber distal end 201 is coplanar with tube distal end 401 when an assembled adjustable illumination probe comprises an assembled adjustable illumination probe with retracted tube 1401, e.g., optic fiber 200 may be disposed in tube 400 wherein optic fiber distal end 201 is flush with tube distal end 401 when an assembled adjustable illumination probe comprises an assembled adjustable illumination probe with retracted tube 1401. Illustratively, optic fiber 200 may be disposed in tube 400 wherein optic fiber distal end 201 is adjacent to tube aperture 410 when an assembled adjustable illumination probe comprises an assembled adjustable illumination probe with retracted tube 1401, e.g., optic fiber 200 may be disposed in tube 400 wherein optic fiber distal end 201 abuts tube aperture 410 when an assembled adjustable illumination probe comprises an assembled adjustable illumination probe with retracted tube 1401. In one or more embodiments, optic fiber 200 may be disposed in tube 400 wherein optic fiber distal end 201 is coplanar with tube aperture 410 when an assembled adjustable illumination probe comprises an assembled adjustable illumination probe with retracted tube 1401, e.g., optic fiber 200 may be disposed in tube 400 wherein optic fiber distal end 201 is flush with tube aperture 410 when an assembled adjustable illumination probe comprises an assembled adjustable illumination probe with retracted tube 1401. Illustratively, optic fiber 200 may be disposed in tube 400 wherein a portion of optic fiber 200 is disposed in tube aperture 410 when an assembled adjustable illumination probe comprises an assembled adjustable illumination probe with retracted tube 1401, e.g., optic fiber 200 may be disposed in tube 400 wherein optic fiber distal end 201 is disposed in tube aperture 410 when an assembled adjustable illumination probe comprises an assembled adjustable illumination probe with retracted tube 1401.

Figure 15:
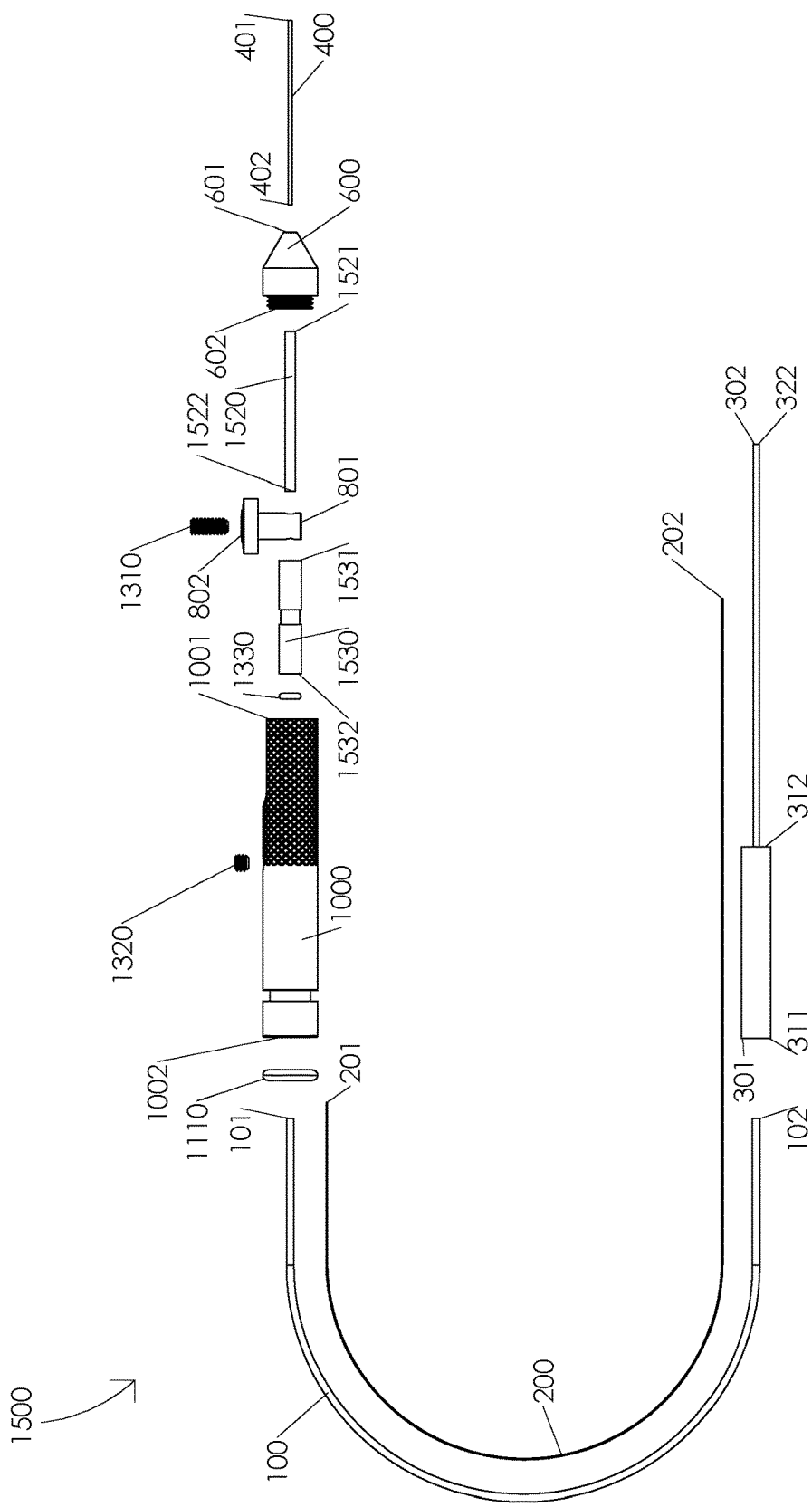
FIG. 15 is a schematic diagram illustrating an exploded view of an adjustable illumination probe assembly.

FIG. 15 is a schematic diagram illustrating an exploded view of an adjustable illumination probe assembly 1500. In one or more embodiments, an adjustable illumination probe assembly 1500 may comprise a jacketing 100, an optic fiber 200, an illumination source connector 300, a tube 400, a nosecone 600, a piston tube 1520, a control mechanism 800, a piston tube guide 1530, an adjustable handle 1000, an identification ring, 1110, a first fixation mechanism 1310, a second fixation mechanism 1320, and a hermetic seal ring 1330.

Figure 16A:
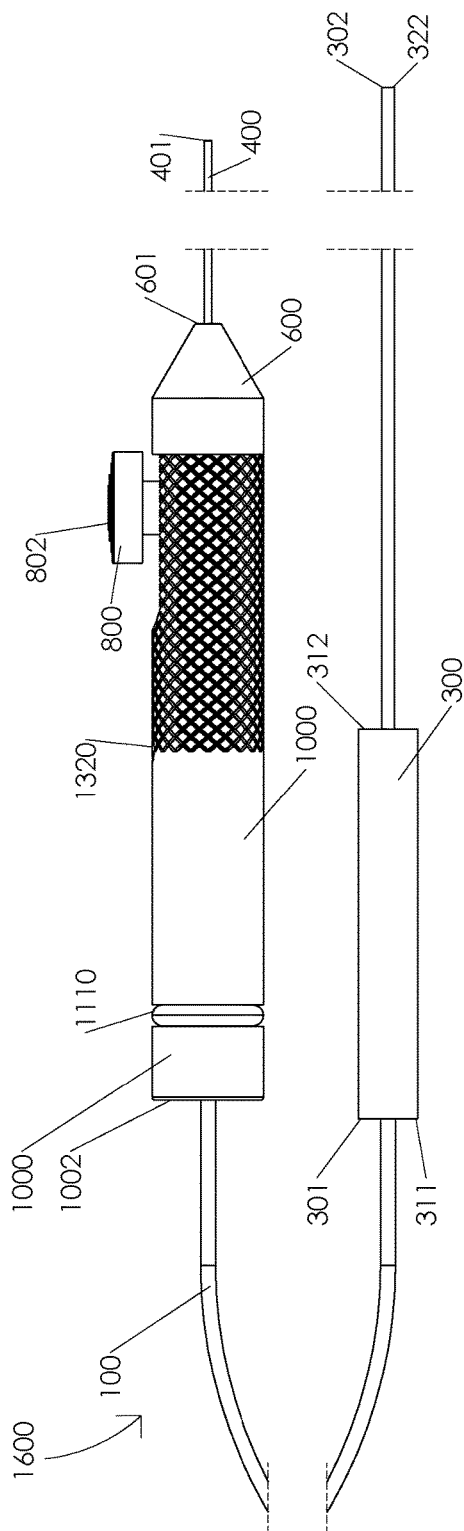
FIGS. 16A, 16B, 16C, and 16D are schematic diagrams illustrating an assembled adjustable illumination probe.
Figure 16B:
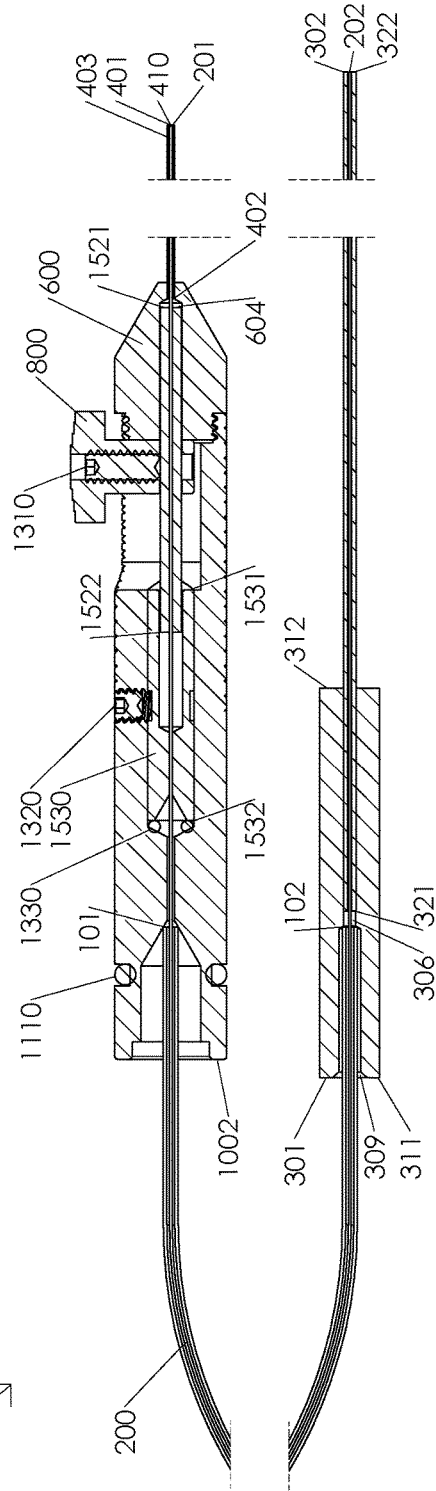
Figures 16C, 16D:
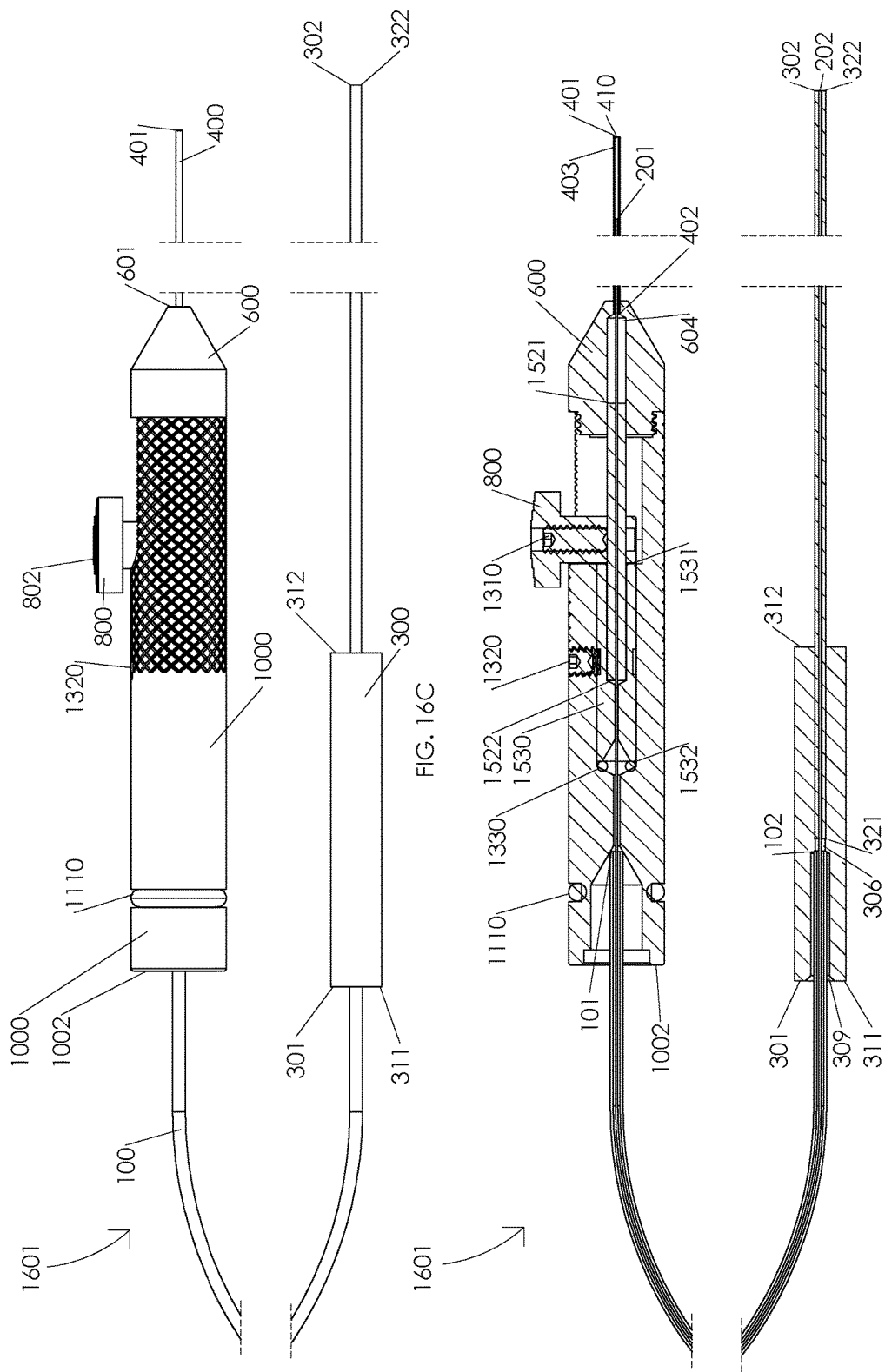

FIGS. 16A, 16B, 16C, and 16D are schematic diagrams illustrating an assembled adjustable illumination probe. FIG. 16A illustrates a side view of an assembled adjustable illumination probe with extended optic fiber 1600. FIG. 16B illustrates a cross-sectional view in a sagittal plane of an assembled adjustable illumination probe with extended optic fiber 1600. FIG. 16C illustrates a side view of an assembled adjustable illumination probe with retracted optic fiber 1601. FIG. 16D illustrates a cross-sectional view in a sagittal plane of an assembled adjustable illumination probe with retracted optic fiber.

In one or more embodiments, a portion of optic fiber 200 may be disposed in jacketing 100, e.g., a portion of optic fiber 200 may be disposed in jacketing inner diameter 103. Illustratively, optic fiber 200 may be disposed in jacketing 100 wherein optic fiber distal end 201 extends out from jacketing distal end 101. In one or more embodiments, optic fiber 200 may be disposed in jacketing 100 wherein optic fiber proximal end 202 extends out from jacketing proximal end 102. Illustratively, a portion of optic fiber 200 may be fixed in a portion of jacketing 100, e.g., a portion of optic fiber 200 may be fixed in a portion of jacketing 100 by an interference fit, an adhesive, an epoxy, a setscrew, a crimp, etc. In one or more embodiments, a portion of jacketing 100 may be disposed in a portion of illumination source connector 300, e.g., jacketing proximal end 102 may be disposed in connector base distal inner bore 308. Illustratively, a portion of jacketing 100 may be fixed in a portion of illumination source connector 300, e.g., a portion of jacketing 100 may be fixed in a portion of illumination source connector 300 by an interference fit, an adhesive, an epoxy, a setscrew, a tie, a crimp, a weld, etc. In one or more embodiments, a portion of optic fiber 200 may be disposed in illumination source connector 300, e.g., optic fiber proximal end 202 may be disposed in illumination source connector 300. Illustratively, optic fiber 200 may be disposed in connector base distal taper 309, connector base distal inner bore 308, connector base proximal taper 307, connector base proximal inner bore 306, and optic fiber housing inner bore 305. In one or more embodiments, optic fiber 200 may be disposed in illumination source connector 300 wherein optic fiber proximal end 202 is adjacent to illumination source connector proximal end 302, e.g., optic fiber 200 may be disposed in illumination source connector 300 wherein optic fiber proximal end 202 is adjacent to optic fiber housing proximal end 322. Illustratively, optic fiber 200 may be disposed in illumination source connector 300 wherein optic fiber proximal end 202 abuts illumination source connector proximal end 302, e.g., optic fiber 200 may be disposed in illumination source connector 300 wherein optic fiber proximal end 202 abuts optic fiber housing proximal end 322. In one or more embodiments, optic fiber 200 may be disposed in illumination source connector 300 wherein optic fiber proximal end 202 is coplanar with illumination source connector proximal end 302, e.g., optic fiber 200 may be disposed in illumination source connector 300 wherein optic fiber proximal end 202 is coplanar with optic fiber housing proximal end 322. Illustratively, a portion of optic fiber 200 may be fixed in a portion of illumination source connector 300, e.g., a portion of optic fiber 200 may be fixed in a portion of illumination source connector 300 by an interference fit, an adhesive, an epoxy, a setscrew, a crimp, etc.

In one or more embodiments, a portion of nosecone 600 may be disposed in a portion of adjustable handle 1000, e.g., nosecone proximal end 602 may be disposed in adjustable handle 1000. Illustratively, a portion of nosecone 600 may be disposed in a portion of adjustable handle 1000 wherein nosecone distal end 601 extends out from adjustable handle distal end 1001. In one or more embodiments, a portion of nosecone 600 may be fixed in a portion of handle 1000, e.g., a portion of nosecone 600 may be fixed in a portion of handle 1000 by an interference fit, an adhesive, an epoxy, a setscrew, a tie, a crimp, a weld, a threading, etc. Illustratively, nosecone threading 610 and adjustable handle threading 1025 may be configured to fix a portion of nosecone 600 in a portion of adjustable handle 1000. In one or more embodiments, identification ring 1110 may be disposed in identification ring housing 1021. Illustratively, identification ring 1110 may be fixed in identification ring housing 1021, e.g., identification ring 1110 may be fixed in identification ring housing 1021 by a force of friction, an adhesive, and epoxy, etc.

In one or more embodiments, piston tube guide 1530 may be disposed in adjustable handle 1000, e.g., piston tube guide 1530 may be disposed in piston tube guide housing 1009. Illustratively, piston tube guide 1530 may be disposed in piston tube guide housing 1009 wherein piston tube guide proximal end 1532 is adjacent to adjustable handle distal taper 1008, e.g., piston tube guide 1530 may be disposed in piston tube guide housing 1009 wherein piston tube guide proximal end 1532 abuts handle distal taper 1008. In one or more embodiments, piston tube guide 1530 may be disposed in piston tube guide housing 1009 wherein piston tube guide distal end 1531 is adjacent to control mechanism base proximal interface 1030, e.g., piston tube guide 1530 may be disposed in piston tube guide housing 1009 wherein piston tube guide distal end 1531 abuts control mechanism base proximal interface 1030. Illustratively, piston tube guide 1530 may be fixed in piston tube guide housing 1009, e.g., piston tube guide 1530 may be fixed in piston tube guide housing 1009 by an interference fit, an adhesive, an epoxy, a setscrew, a tie, a crimp, a weld, a threading, etc. In one or more embodiments, second fixation mechanism 1320 may be configured to fix piston tube guide 1530 in piston tube guide housing 1009, e.g., second fixation mechanism 1320 may be disposed in second fixation mechanism housing 1020. Illustratively, second fixation mechanism 1320 may comprise a setscrew configured to fix piston tube guide 1530 in piston tube guide housing 1009.

In one or more embodiments, hermetic seal ring 1330 may be disposed in adjustable handle distal taper 1008 and piston tube guide proximal taper 903, e.g., hermetic seal ring 1330 may be configured to form a hermetic seal between adjustable handle distal taper 1008 and piston tube guide proximal taper 903. Illustratively, hermetic seal ring 1330 may be fixed in adjustable handle distal taper 1008 and piston tube guide proximal taper 903, e.g., hermetic seal ring 1330 may be fixed in adjustable handle distal taper 1008 and piston tube guide proximal taper 903 by an interference fit, an adhesive, an epoxy, a setscrew, a tie, a crimp, a weld, a threading, etc. In one or more embodiments, piston tube 1520 may be disposed in piston tube guide distal lumen 907, control mechanism housing 1040, piston tube housing 806, and nosecone inner bore 605. Illustratively, piston tube 1520 may be fixed in piston tube housing 806, e.g., piston tube 1520 may be fixed in piston tube housing 806 by an interference fit, an adhesive, an epoxy, a setscrew, a tie, a crimp, a weld, a threading, etc. In one or more embodiments, first fixation mechanism 1310 may be configured to fix piston tube 1520 in piston tube housing 806, e.g., first fixation mechanism 1310 may be disposed in first fixation mechanism housing 805. Illustratively, first fixation mechanism 1310 may comprise a setscrew configured to fix piston tube 1520 in piston tube housing 806. In one or more embodiments, a portion of control mechanism 800 may be disposed in control mechanism housing 1040, e.g., control mechanism base 815 may be disposed in control mechanism housing 1040. Illustratively, a portion of control mechanism 800 may be fixed in control mechanism housing 1040, e.g., first fixation mechanism 1310 may be configured to fix a portion of control mechanism 800 in control mechanism housing 1040 by fixing piston tube 1520 in piston tube housing 806. For example, a length of piston tube 1520 may be configured to fix a portion of control mechanism 800 in control mechanism housing 1040. In one or more embodiments, piston tube 1520 may be configured to actuate proximally and distally within piston tube guide distal lumen 907, control mechanism housing 1040, and nosecone inner bore 605. Illustratively, a portion of control mechanism 800 may be configured to actuate proximally and distally within control mechanism housing 1040. In one or more embodiments, an actuation of control mechanism 800 within control mechanism housing 1040 may be configured to actuate piston tube 1520 within piston tube guide distal lumen 907, control mechanism housing 1040, and nosecone inner bore 605.

Illustratively, a portion of tube 400 may be disposed in nosecone 600, e.g., a portion of tube 400 may be disposed in tube guide 603. In one or more embodiments, a portion of tube 400 may be disposed in nosecone 600 wherein tube distal end 401 extends out from nosecone distal end 601. Illustratively, a portion of tube 400 may be fixed in nosecone 600, e.g., a portion of tube 400 may be fixed in tube guide 603 by an interference fit, an adhesive, an epoxy, a setscrew, a tie, a crimp, a weld, a threading, etc. In one or more embodiments, a portion of jacketing 100 may be disposed in a portion of adjustable handle 1000, e.g., jacketing distal end 101 may be disposed in adjustable handle medial chamber 1005. Illustratively, a portion of jacketing 100 may be fixed in a portion of adjustable handle 1000, e.g., a portion of jacketing 100 may be fixed in a portion of adjustable handle 1000 by an interference fit, an adhesive, an epoxy, a setscrew, a tie, a crimp, a weld, a threading, etc.

In one or more embodiments, a portion of optic fiber 200 may be disposed in adjustable handle 1000, nosecone 600, and tube 400. Illustratively, optic fiber 200 may be disposed in adjustable handle proximal taper 1003, adjustable handle proximal chamber 1004, adjustable handle medial chamber 1005, adjustable handle medial taper 1006, adjustable handle distal chamber 1007, adjustable handle distal taper 1008, piston tube guide housing 1009, piston tube lumen 710, control mechanism housing 1040, control mechanism 800, nosecone proximal taper 606, nosecone inner bore 605, nosecone distal taper 604, tube guide 603, and optic fiber guide 403. In one or more embodiments, a portion of optic fiber 200 may be fixed in piston tube lumen 710 wherein an actuation of piston tube 1520 is configured to actuate optic fiber 200. In one or more embodiments, a portion of optic fiber 200 may be fixed in a position relative to piston tube 1520. Illustratively, a portion of optic fiber 200 may be fixed in a position relative to piston tube 1520 by an interference fit, an adhesive, an epoxy, a setscrew, a tie, a crimp, a weld, a threading, etc. In one or more embodiments, an actuation of control mechanism 800 towards adjustable handle distal end 1001 and away from adjustable handle proximal end 1002 may be configured to extend piston tube 1520 relative to adjustable handle 1000. Illustratively, an extension of piston tube 1520 relative to adjustable handle 1000 may be configured to extend optic fiber 200 relative to tube 400. In one or more embodiments, optic fiber 200 may be fully extended relative to tube 400 when an assembled adjustable illumination probe comprises an assembled adjustable illumination probe with extended optic fiber 1600. Illustratively, an actuation of control mechanism 800 towards adjustable handle proximal end 1002 and away from adjustable handle distal end 1001 may be configured to retract piston tube 1520 relative to adjustable handle 1000. In one or more embodiments, a retraction of piston tube 1520 relative to adjustable handle 1000 may be configured to retract optic fiber 200 relative to tube 400. Illustratively, optic fiber 200 may be fully retracted relative to tube 400 when an assembled adjustable illumination probe comprises an assembled adjustable illumination probe with retracted optic fiber 1601.

Illustratively, optic fiber 200 may be disposed in tube 400 wherein optic fiber distal end 201 is not adjacent to tube distal end 401 when an assembled adjustable illumination probe comprises an assembled adjustable illumination probe with retracted optic fiber 1601, e.g., optic fiber 200 may be disposed in tube 400 wherein optic fiber distal end 201 does not abut tube distal end 401 when an assembled adjustable illumination probe comprises an assembled adjustable illumination probe with retracted optic fiber 1601. In one or more embodiments, optic fiber 200 may be disposed in tube 400 wherein optic fiber distal end 201 is not coplanar with tube distal end 401 when an assembled adjustable illumination probe comprises an assembled adjustable illumination probe with retracted optic fiber 1601, e.g., optic fiber 200 may be disposed in tube 400 wherein optic fiber distal end 201 is not flush with tube distal end 401 when an assembled adjustable illumination probe comprises an assembled adjustable illumination probe with retracted optic fiber 1601. Illustratively, optic fiber 200 may be disposed in tube 400 wherein optic fiber distal end 201 is not adjacent to tube aperture 410 when an assembled adjustable illumination probe comprises an assembled adjustable illumination probe with retracted optic fiber 1601, e.g., optic fiber 200 may be disposed in tube 400 wherein optic fiber distal end 201 does not abut tube aperture 410 when an assembled adjustable illumination probe comprises an assembled adjustable illumination probe with retracted optic fiber 1601. In one or more embodiments, optic fiber 200 may be disposed in tube 400 wherein optic fiber distal end 201 is not coplanar with tube aperture 410 when an assembled adjustable illumination probe comprises an assembled adjustable illumination probe with retracted optic fiber 1601, e.g., optic fiber 200 may be disposed in tube 400 wherein optic fiber distal end 201 is not flush with tube aperture 410 when an assembled adjustable illumination probe comprises an assembled adjustable illumination probe with retracted optic fiber 1601. Illustratively, optic fiber 200 may be disposed in tube 400 wherein a portion of optic fiber 200 is not disposed in tube aperture 410 when an assembled adjustable illumination probe comprises an assembled adjustable illumination probe with retracted optic fiber 1601, e.g., optic fiber 200 may be disposed in tube 400 wherein optic fiber distal end 201 is not disposed in tube aperture 410 when an assembled adjustable illumination probe comprises an assembled adjustable illumination probe with retracted optic fiber 1601.

Illustratively, optic fiber 200 may be disposed in tube 400 wherein optic fiber distal end 201 is adjacent to tube distal end 401 when an assembled adjustable illumination probe comprises an assembled adjustable illumination probe with extended optic fiber 1600, e.g., optic fiber 200 may be disposed in tube 400 wherein optic fiber distal end 201 abuts tube distal end 401 when an assembled adjustable illumination probe comprises an assembled adjustable illumination probe with extended optic fiber 1600. In one or more embodiments, optic fiber 200 may be disposed in tube 400 wherein optic fiber distal end 201 is coplanar with tube distal end 401 when an assembled adjustable illumination probe comprises an assembled adjustable illumination probe with extended optic fiber 1600, e.g., optic fiber 200 may be disposed in tube 400 wherein optic fiber distal end 201 is flush with tube distal end 401 when an assembled adjustable illumination probe comprises an assembled adjustable illumination probe with extended optic fiber 1600. Illustratively, optic fiber 200 may be disposed in tube 400 wherein optic fiber distal end 201 is adjacent to tube aperture 410 when an assembled adjustable illumination probe comprises an assembled adjustable illumination probe with extended optic fiber 1600, e.g., optic fiber 200 may be disposed in tube 400 wherein optic fiber distal end 201 abuts tube aperture 410 when an assembled adjustable illumination probe comprises an assembled adjustable illumination probe with extended optic fiber 1600. In one or more embodiments, optic fiber 200 may be disposed in tube 400 wherein optic fiber distal end 201 is coplanar with tube aperture 410 when an assembled adjustable illumination probe comprises an assembled adjustable illumination probe with extended optic fiber 1600, e.g., optic fiber 200 may be disposed in tube 400 wherein optic fiber distal end 201 is flush with tube aperture 410 when an assembled adjustable illumination probe comprises an assembled adjustable illumination probe with extended optic fiber 1600. Illustratively, optic fiber 200 may be disposed in tube 400 wherein a portion of optic fiber 200 is disposed in tube aperture 410 when an assembled adjustable illumination probe comprises an assembled adjustable illumination probe with extended optic fiber 1600, e.g., optic fiber 200 may be disposed in tube 400 wherein optic fiber distal end 201 is disposed in tube aperture 410 when an assembled adjustable illumination probe comprises an assembled adjustable illumination probe with extended optic fiber 1600.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of an illumination probe, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
a handle having a handle distal end and a handle proximal end;
an illumination source connector having an illumination source connector distal end and an illumination source connector proximal end;
a tube having a tube distal end and a tube proximal end;
an tube aperture of the tube distal end wherein the tube aperture has a generally rectangular geometry having a width in a range of 0.00314 to 0.0320 inches and a height in a range of 0.00314 to 0.0320 inches; and
an optic fiber having an optic fiber distal end and an optic fiber proximal end, the optic fiber disposed in the illumination source connector, the handle, and the tube.

2. The instrument of claim 1 further comprising:
a piston tube having a piston tube distal end and a piston tube proximal end, the piston tube disposed in the handle.

3. The instrument of claim 2 further comprising:
a piston tube guide having a piston tube guide distal end and a piston tube guide proximal end, the piston tube guide disposed in the handle wherein at least a portion of the piston tube is disposed in the piston tube guide.

4. The instrument of claim 3 further comprising:
a control mechanism having a control mechanism distal end and a control mechanism proximal end, the control mechanism at least partially disposed in the handle wherein the piston tube is disposed in a piston tube housing of the control mechanism.

5. The instrument of claim 4 wherein a portion of the optic fiber is fixed in the piston tube.

6. The instrument of claim 4 wherein a portion of the tube is fixed in the piston tube.

7. The instrument of claim 1 wherein the tube aperture comprises a heatsink.

8. The instrument of claim 1 wherein the tube aperture comprises an optical filter.

9. The instrument of claim 1 wherein the tube aperture comprises a lens.

10. The instrument of claim 9 wherein the tube aperture comprises a biconvex lens.

11. The instrument of claim 9 wherein the tube aperture comprises a biconcave lens.

12. The instrument of claim 9 wherein the tube aperture comprises a plano-convex lens.

13. The instrument of claim 9 wherein the tube aperture comprises a plano-concave lens.

14. The instrument of claim 9 wherein the tube aperture comprises a negative meniscus lens.

15. The instrument of claim 9 wherein the tube aperture comprises a positive meniscus lens.

16. An instrument comprising:
a handle having a handle distal end and a handle proximal end;
an illumination source connector having an illumination source connector distal end and an illumination source connector proximal end;
a piston tube having a piston tube distal end and a piston tube proximal end, the piston tube disposed in the handle;
a piston tube guide having a piston tube guide distal end and a piston tube guide proximal end, the piston tube guide disposed in the handle wherein at least a portion of the piston tube is disposed in the piston tube guide;
a control mechanism having a control mechanism distal end and a control mechanism proximal end, the control mechanism at least partially disposed in the handle wherein the piston tube is disposed in a piston tube housing of the control mechanism;
a tube having a tube distal end and a tube proximal end;
a tube aperture of the tube distal end, the tube aperture having a generally rectangular geometry; and
an optic fiber having an optic fiber distal end and an optic fiber proximal end, the optic fiber disposed in the illumination source connector, the handle, and the tube.

17. The instrument of claim 16 wherein at least a portion of the optic fiber is fixed in the piston tube.

18. The instrument of claim 16 wherein at least a portion of the tube is fixed in the piston tube.

19. The instrument of claim 16 wherein the tube aperture comprises an optical filter.

20. The instrument of claim 16 wherein the tube aperture comprises a lens.

* * * * *